(12) United States Patent
Crawford et al.

(10) Patent No.: US 7,332,605 B2
(45) Date of Patent: Feb. 19, 2008

(54) PROCESS FOR THE SYNTHESIS OF CXCR4 ANTAGONIST

(75) Inventors: Jason B. Crawford, British Columbia (CA); Gang Chen, British Columbia (CA); David Gauthier, British Columbia (CA); Renato Skerlj, Vancouver (CA); Ian R. Baird, Abbotsford (CA); Trevor R. Wilson, Langley (CA)

(73) Assignee: AnorMED, Inc., Langley (CA)

( * ) Notice: Subject to any disclaimer, the term of this patent is extended or adjusted under 35 U.S.C. 154(b) by 322 days.

(21) Appl. No.: 11/077,896

(22) Filed: Mar. 11, 2005

(65) Prior Publication Data

US 2005/0209277 A1    Sep. 22, 2005

Related U.S. Application Data

(60) Provisional application No. 60/553,589, filed on Mar. 15, 2004.

(51) Int. Cl.
 *C07D 215/38* (2006.01)
(52) U.S. Cl. ..................................... 546/171
(58) Field of Classification Search ................. 546/171
 See application file for complete search history.

(56) References Cited

U.S. PATENT DOCUMENTS

| 5,583,131 A | 12/1996 | Bridger et al. | |
|---|---|---|---|
| 5,698,546 A | 12/1997 | Bridger et al. | |
| 5,817,807 A | 10/1998 | Bridger et al. | |
| 6,734,194 B2 * | 5/2004 | End et al. | 514/312 |
| 6,864,265 B2 * | 3/2005 | Bridger et al. | 514/314 |
| 7,091,217 B2 * | 8/2006 | Bridger et al. | 514/311 |

FOREIGN PATENT DOCUMENTS

| WO | WO-00/56729 | 9/2000 |
|---|---|---|
| WO | WO-03/055876 | 7/2003 |

OTHER PUBLICATIONS

Carroll et al., Science (1997) 276:274-276.
Lukacs et al., Am. J. Pathology (2002) 160:1353-1360.
International Search Report for PCT/US05/08268, mailed on May 26, 2005, 4 pages.
Matthys et al., J. Immunol. (2001) 107:4686-4692.
Ponath, Exp. Opin. Invest. Drugs (1998) 7:1-18.
Schols et al., Presented at the 9th Conference on Retroviruses and Opportunistic Infections, Feb. 24-28, 2002, Washington State Convention and Trade Center, Seattle, Washington.

* cited by examiner

*Primary Examiner*—D. Margaret Seaman
(74) *Attorney, Agent, or Firm*—Morrison & Foerster LLP

(57) ABSTRACT

This invention relates to a process for synthesizing heterocyclic pharmaceutical compound which binds to the CXCR4 chemokine receptor. In one embodiment, the process comprises: a) reacting a 5,6,7,8-tetrahydroquinolinylamine and an alkyl aldehyde bearing a phthalimide or a di-tertiary-butoxycarbonyl (di-BOC) protecting group to form an imine; b) reducing the imine to form a secondary amine; c) reacting the secondary amine with a haloalkyl substituted heterocyclic compound, to form a phthalimido-protected or di-tert-butoxycarbonyl protected tertiary amine; and d) hydrolyzing the protected amine to obtain a compound having Formula I'

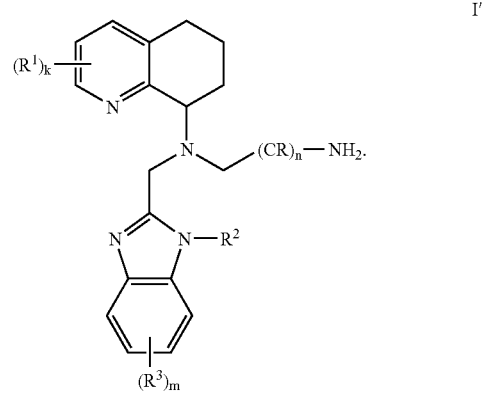

38 Claims, No Drawings

PROCESS FOR THE SYNTHESIS OF CXCR4 ANTAGONIST

CROSS REFERENCE TO RELATED APPLICATIONS

This application claims priority to U.S. provisional patent application Ser. No. 60/553,589, filed Mar. 15, 2004, which is incorporated by reference in this application.

TECHNICAL FIELD

This invention relates to a process for synthesizing heterocyclic pharmaceutical compounds which bind to the CXCR4 chemokine receptor.

BACKGROUND OF THE INVENTION

It is desired by those with skill in the art to develop efficient and reliable synthetic routes to pure and stable forms of pharmaceutical compounds. As examples, the novel heterocyclic compounds disclosed in WO 0056729 demonstrate protective effects against infection of target cells by human immunodeficiency virus (HIV).

The chemotactic cytokines, or chemokines, are a family of proteins, approximately 8-10 kDa in size that function, at least in part by modulating a complex and overlapping set of biological activities important for the movement of lymphoid cells and extravasation and tissue infiltration of leukocytes in response to inciting agents (see, for example: P. Ponath, *Exp. Opin. Invest. Drugs*, 7:1-18, 1998). The cellular receptors for these proteins are classified based on the chemokine natural ligand. Receptors of the β-chemokines are designated with the prefix "CCR," whereas the receptors of the α-chemokine are designated with the prefix "CXCR".

The natural chemokine ligand for the CXCR4 receptor is stromal cell-derived factor-1 (SDF-1). The inhibition of the binding of SDF-1 to CXCR4 by specific small-molecule inhibitors has been shown in a model, to reduce the severity of the pathogenesis of collagen II-induced arthritis (Matthys et al., *J. Immunol.* 107: 4686-4692, 2001). This model, which is used as a study model for the pathogenesis of rheumatoid arthritis in humans, shows that SDF-1 plays a central role in the pathogenesis of murine collagen induced arthritis. Similarly, the use of small-molecule CXCR4 inhibitors has been shown in a murine model, to reduce a number of pathological parameters related to asthmatic-type inflammation in an allergin-induced inflammation (Lukacs et al., *Am. J. Pathology*, 160 (4): 1353-1360, 2002).

Two specific chemokine receptors, CXCR4 and CCR5, have been implicated in the etiology of infection by human immunodeficiency virus (HIV). The T cell-line tropic (T-tropic) viral phenotype of HIV requires, for infection, an association with the CXCR4 receptor, which is expressed in the surface of certain cells of the immune system (Carroll et al., *Science*, 276: 274-276, 1997). Specifically, an interaction between HIV and the CXCR-4 receptor is required for membrane fusion, a necessary step in the infection of the host immune cell.

The novel heterocyclic compounds disclosed in U.S. Pat. Nos. 5,583,131, 5,698,546 and 5,817,807 selectively bind to the CXCR4 receptor, inhibiting the binding of the natural SDF-1 ligand. Such binding may show anti-inflammatory effects. The binding also competitively prevents the binding of the T-tropic HIV with the receptor, and thus imparts a preventative effect against HIV infection.

The compound AMD3100, which is a specific CXCR4 antagonist, has been shown to reduce HIV viral load and X4 (T-tropic) virus levels in humans (D. Schols et al. Presented at: 9th Conference on Retroviruses and Opportunistic Infections, Feb. 24-28, 2002, Washington State Convention and Trade Center, Seattle, Wash.).

This invention describes the processes for the efficient synthesis and isolation of pure forms of these compounds.

SUMMARY OF THE INVENTION

The invention provides a process for synthesizing heterocyclic pharmaceutical compounds which bind to the CXCR4 chemokine receptor. In a particular embodiment, the invention provides a process for synthesizing an optionally substituted (R), (S) or (RS) (N'-(1H-benzimidazol-2-ylmethyl)-N'-5,6,7,8-tetrahydroquinolin-8-yl-1,4-alkylamine) having formula I'

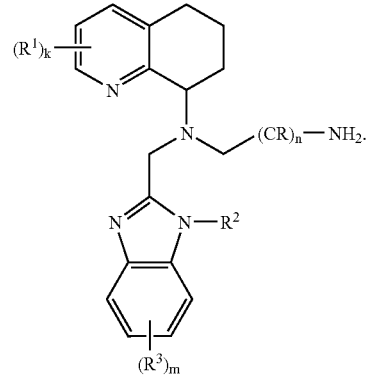

Generally, the process comprises: a) reacting a 5,6,7,8-tetrahydroquinolinylamine with an alkyl aldehyde bearing a phthalimido or a di-tertiary-butoxycarbonyl (di-BOC) protecting group to form an imine; b) reducing the imine to form a secondary amine; c) reacting the secondary amine with a haloalkyl substituted heterocyclic compound; and d) removing the amino-protecting groups. Optional steps include a decolorizing and/or purifying treatment, and a process for the crystallization of the compound.

In Formula I', R, $R^1$, $R^2$ and $R^3$ are non-interfering substituents; k is 0-3; m is 0-4 and n is 1-6. In one embodiment, R, $R^1$, $R^2$ and $R^3$ are each independently selected from the group consisting of hydrogen, halo, nitro, cyano, a protected carboxylic acid, alkyl, alkenyl, cycloalkyl, a protected hydroxyl, a protected thiol, a protected amino, acyl, carboxylate, carboxamide, sulfonamide, an aromatic group and a heterocyclic group. In addition, R, $R^1$, $R^2$ and $R^3$ may be absent. By "protected," it is meant that the group is rendered unreactive by protecting it with an additional nonreactive chemical moiety which may later be selectively removed.

More particularly, when the non-interfering substituent is alkyl, alkenyl or cycloalkyl, it may be alkyl($C_{1-10}$), alkenyl ($C_{2-10}$), alkynyl($C_{2-10}$), aryl($C_{5-12}$), arylalkyl, arylalkenyl, or arylalkynyl, each of which may optionally contain one or more heteroatoms selected from O, S, and N and each of which may further be substituted; or optionally substituted forms of acyl, arylacyl, alkyl- alkenyl-, alkynyl- or arylsulfonyl and forms thereof which contain heteroatoms in the alkyl, alkenyl, alkynyl or aryl moieties. Other noninterfering substituents include OR, SR, $NR_2$, COOR, $CONR_2$, where R is H or alkyl, alkenyl, alkynyl or aryl as defined above. Where the substituted atom is C, the substituents may include, in addition to the substituents listed above, halo, OOCR, NROCR, where an R is H or a substituent set forth above, or may be =O.

In general, a "noninterfering substituent" is a substituent whose presence does not destroy the ability of the compound of Formula I' to behave as a chemokine antagonist. Specifically, the presence of the substituent does not destroy the effectiveness of the compound. Because the compounds of the present invention have been shown to inhibit HIV replication, and have been shown to have anti-inflammatory effects by specifically interacting with the CXCR4 receptor, the compounds of the invention are effective in treating conditions which require modulation of CXCR4 mediated activity.

In one aspect, the invention provides a method for synthesizing a compound having Formula I', comprising:
a) reacting an optionally substituted ($R^1$) 5,6,7,8-tetrahydroquinolinylamine ((R), (S) or (R,S)) with an alkyl aldehyde bearing a phthalimide protecting group or a di-tert-butoxycarbonyl (di-BOC) protecting group in an organic solvent with or without a dehydrating agent to produce an imine;
b) reducing the imine in an organic solvent with a metal hydride reducing reagent in the presence of an organic acid or a metal salt to form a secondary amine;
c) reacting the secondary amine with an optionally substituted 2-halomethylbenzimidazole optionally bearing a benzimidazole amine protecting group or other amine substituent in an organic solvent to form a phthalimido-protected or di-tert-butoxycarbonyl-protected tertiary amine; and
d) hydrolyzing the protected tertiary amine to obtain a compound having Formula IA'.

In one example as shown in Scheme 1, step a) comprises reacting an optionally substituted ($R^1$) 5,6,7,8-tetrahydroquinolinylamine ((R), (S) or (RS)) with an alkyl aldehyde bearing a phthalimide protecting group having Formula III' (or a 1,3-dioxo-1,3-dihydroisoindol-2-yl)-alkyl aldehyde) to form an imine having Formula IV' via condensation (Scheme 1a). Alternatively, the alkyl aldehyde may bear a di-BOC protecting group having Formula IIa' to form an imine having Formula IVa' via condensation (Scheme 1b). The alkyl aldehyde is preferably an ethyl aldehyde, a propyl aldehyde, a butyl aldehyde or a pentyl aldehyde.

In another example as shown in Scheme 2, step b) comprises reducing an imine having Formula IV' in an organic solvent with a metal hydride reducing reagent and either an organic acid or a metal salt to form an N-[(1,3-dioxo-1,3-dihydroisoindol-2-yl)-alkyl]-tetrahydroquinolinylamine having Formula V' (Scheme 2a). Alternatively, an imine having Formula IVa' may be reduced to form a secondary amine hydrochloride salt having Formula Va' (Scheme 2b).

Scheme 1

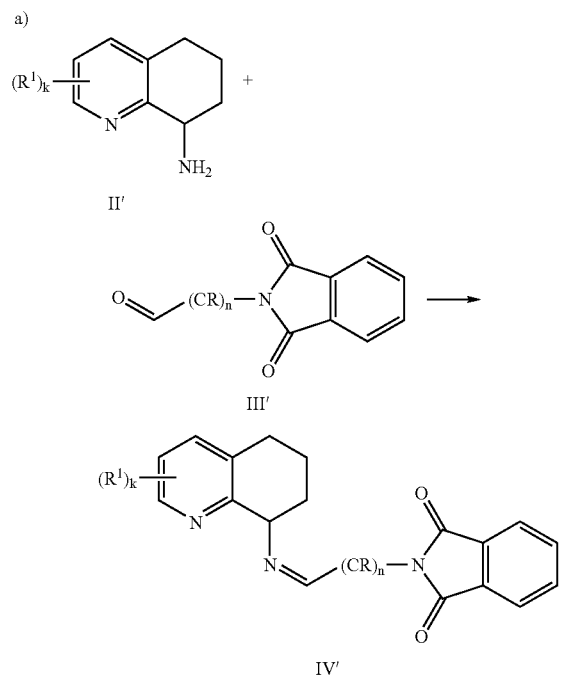

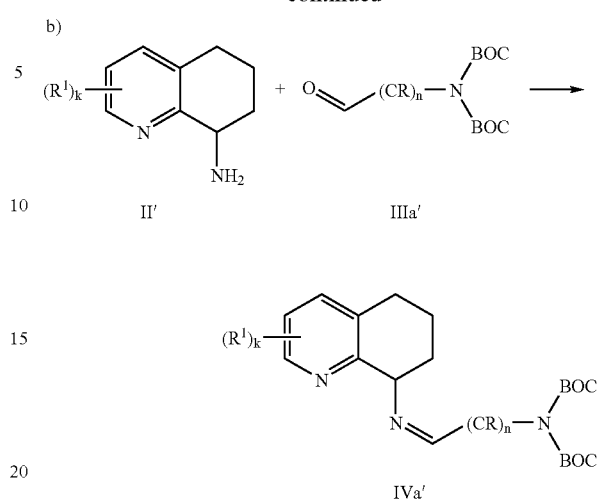

Scheme 2

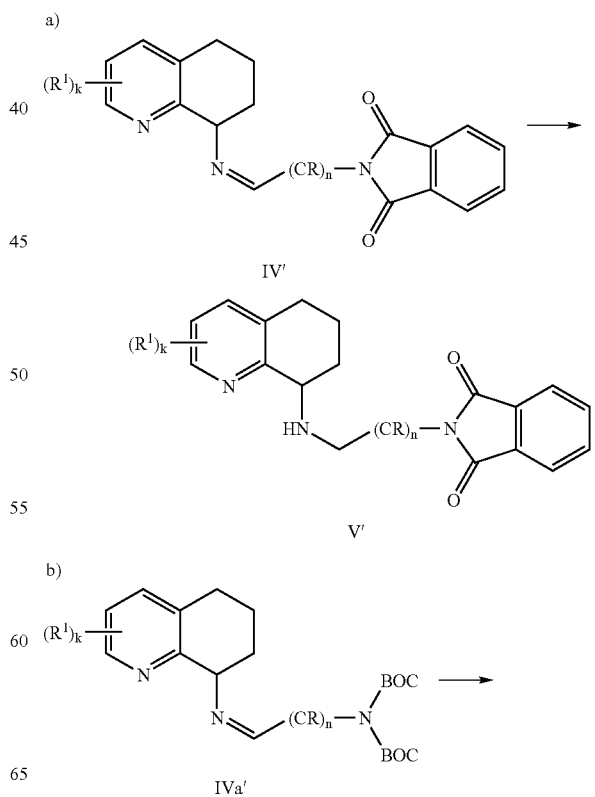

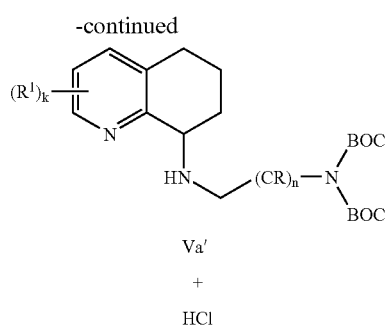

Va'

+

HCl

In yet another example as shown in Scheme 3, step c) comprises reacting a secondary amine having formula V' (N-[(1,3-dioxo-1,3-dihydroisoindol-2-yl)-alkyl]-tetrahydro-quinolinylamine) with an optionally substituted ($R^3$) 2-halomethylbenzimidazole (Formula VI'). In one example, step c) comprises reacting the secondary amine with 2-halomethylbenzimidazole in an organic solvent at elevated temperature under basic conditions to form a N-{[(benzimidazol-2-yl)methyl-(1,3-dioxo-1,3-dihydroisoindol-2-yl)-alkyl]-tetrahydroquinolinyl}amine having Formula VII' (Scheme 3a). Alternatively, alkylation of a secondary amine HCl salt having Formula Va' with a 2-halomethylbenzimidazole as previously described results in a protected tertiary amine having Formula VIIa' (Scheme 3b).

In Formula VI' in Scheme 3, X may be any halo leaving group, such as chlorine, bromine and iodine. The ($R^3$) 2-halomethylbenzimidazole (Formula VI') may further be substituted with a benzimidazole amine protecting group or other amine substituent ($R^2$).

Scheme 3

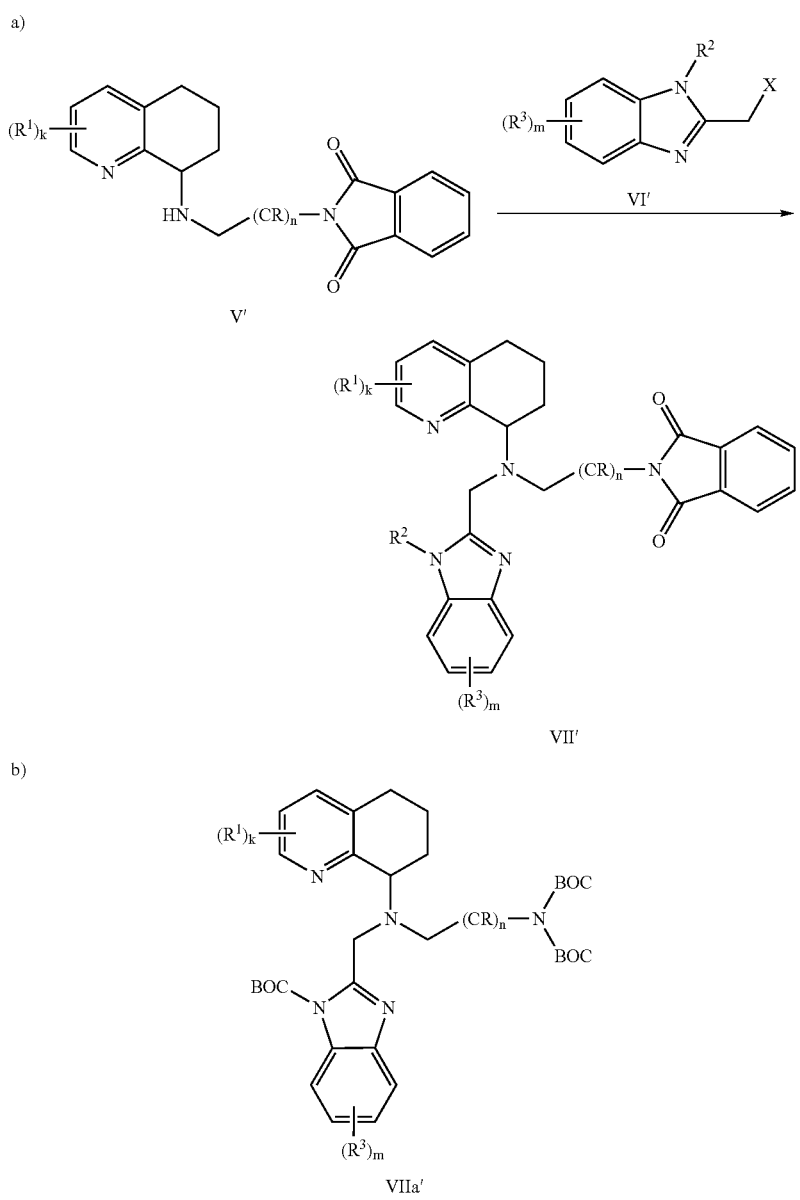

In another example as shown in Scheme 4, step d) comprises sequentially or simultaneously hydrolyzing the benzimidazole amine-protecting group (formula VII' or formula VIIa'), if present, and the phthalimide or di-BOC protecting group to obtain the compound according to Formula I' (Scheme 4).

Scheme 4

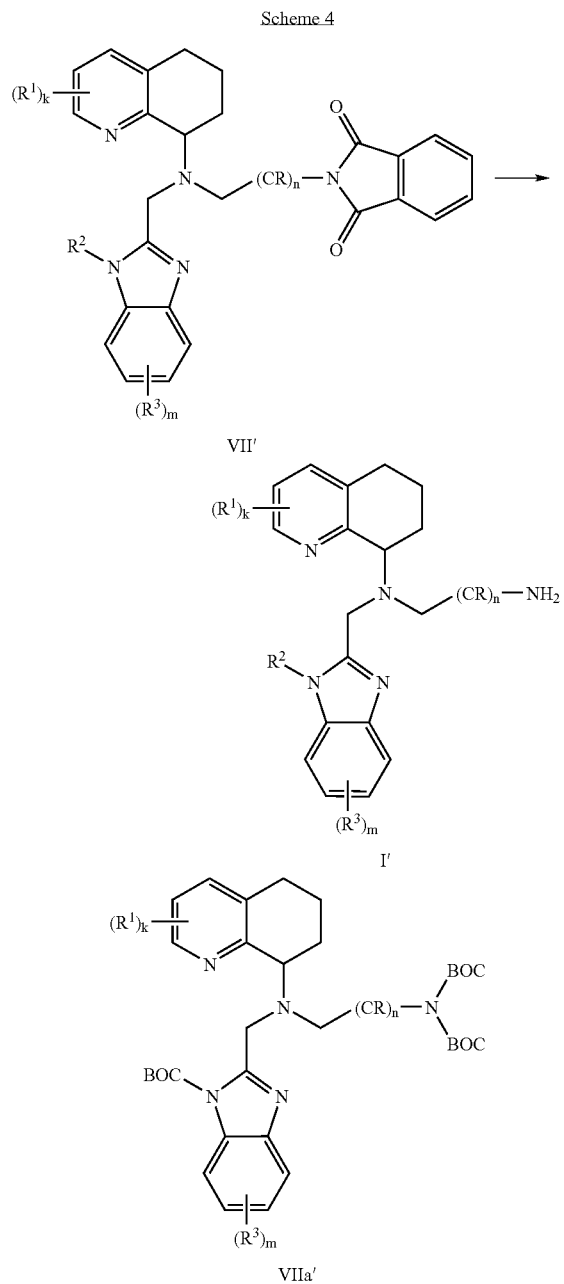

The process of the present invention may further comprise the steps of:
(a) treating the Formula I' compound with decolorizing carbon and silica gel to remove impurities; and
(b) in the case of an optically active Formula I' compound, isolating the N'-(1H-benzimidazol-2-ylmethyl)-N'-5,6,7,8-tetrahydroquinolin-8-yl-alkyldiamine (I') as a crystalline material (as the (R) or (S) enantiomer) via a selective crystallization process.

In an exemplary embodiment, the process is used to synthesize an unsubstituted (S) (N'-(1H-benzimidazol-2-ylmethyl)-N'-5,6,7,8-tetrahydroquinolin-8-yl-1,4-butanediamine) (Formula I). It should be readily apparent to those of ordinary skill in the art that the process remains essentially the same whether the ultimate compound is substituted or not, and/or whether the process results in a product that consists of a single enantiomer or a mixture of enantiomers.

In one aspect as shown in Schemes 5-8, the process for synthesizing a compound having Formula I, comprises:
(a) reacting an unsubstituted (5,6,7,8-tetrahydroquinolin-8-yl)-amine (S) with a 1-(1,3-dioxo-1,3-dihydroisoindol-2-yl)-butan-4-al in an organic solvent in the presence of a metal carbonate salt to produce an imine via a condensation;
(b) reducing the imine in an organic solvent with a metal hydride reducing reagent and either an organic acid or a metal salt to form an a N-{[1-(1,3-dioxo-1,3-dihydroisoindol-2-yl)-butan-4-yl]-(5,6,7,8-tetrahydroquinolin-8-yl)}-amine;
(c) reacting the N-{[1-(1,3-dioxo-1,3-dihydroisoindol-2-yl)-butan-4-yl]-(5,6,7,8-tetrahydroquinolin-8-yl)}-amine with 2-chloromethylbenzimidazole bearing a butoxycarbonyl moiety as the benzimidazole amine protecting group in an organic solvent at elevated temperature under basic conditions to form an N-{[1-(1,3-dioxo-1,3-dihydroisoindol-2-yl)-butan-4-yl]-[(benzimidazol-2-yl)-methyl]-(5,6,7,8-tetrahydroquinolin-8-yl)}-amine; and
(d) sequentially or simultaneously hydrolyzing the benzimidazole amine-protecting group and the phthalimide protecting group to obtain the compound according to Formula I.

DETAILED DESCRIPTION OF THE INVENTION

Many pharmaceutical compounds are produced through multi-step chemical syntheses. Each chemical step in the process should efficiently deliver a pure compound. To achieve this goal, each step must be experimentally optimized to enhance both yields and product purities. There is often a requirement, at the end of the synthesis, for a final purification of the biologically active pharmaceutical compound to ensure that it is free of potentially toxic side products or other impurities.

One of the synthetic components of the novel heterocyclic compounds described in this invention, the optionally substituted 5,6,7,8-tetrahydroquinoline (Skupinska et al., *J. Org. Chem.* 67(22): 7890-7893, 2002), is an optically active compound. The description of the synthesis and isolation of the unsubstituted compound (Formula II) is described in WO 2003022785. "Optically active" denotes the ability of a compound to rotate the plane of plane-polarized light. In each case of optical activity of a pure compound, there are two and only two isomers, called "enantiomers", which have identical physical properties except that they rotate the plane of polarized light in opposite directions in equal amounts. The rotation of one enantiomer will be clockwise, called dextrotatory, abbreviated "D" or (+), and the rotation of the other enantiomer will be counterclockwise, called levorotatory, abbreviated "L" or (−). Additionally, the prefixes R and S, based on the spatial arrangement of substituents about a chiral center, are used to denote absolute stereochemistry. There is no correlation between the nomenclature for absolute stereochemistry and the direction of rotation of plane polarized light. (See, for example, March, J. Advanced Organic Chemistry: Reactions, Mechanisms and Structures, 4th Edition, Chapter 4, John Wiley & Sons, USA, 1992).

The term "enantiomeric excess" or "ee" is related to the term "optical purity" in that both are measurements of the same phenomenon. The value of ee is a percentage measurement of the optical purity, with 100 being a pure single, enantiomer. Hence, a compound that is 95% optically pure is 95% ee. The percent optical purity for a given sample is defined as:

$$\text{Percent optical purity} = \frac{[\alpha] \text{ observed}}{[\alpha] \text{ maximum}} \times 100$$

As shown, $[\alpha]$ observed is the observed angle of rotation of plane polarized light and $[\alpha]$ max is the maximum rotation possible (the rotation that would be observed for a single enantiomer). The enantiomeric excess is also related to absolute configuration, and is measured as the percentage excess of one enantiomer over the other as follows:

$$ee = \frac{[R] - [S]}{[R] + [S]} \times 100 = \%R - \%S$$

Enantiomers of chiral drugs may differ considerably in their pharmacological and toxicological effects because they interact with biological macromolecules, the majority of which are stereoselective (Drayer, *Clin. Pharmacol Ther.* 40:125 (1986)). Hence, it is often desired by those with skill in the art to isolate the drug as a single enantiomer in a pure form. In the case of the 8-amino-5,6,7,8-tetrahydroquinoline, an enzymatic kinetic resolution provides the (S)-enantiomer in high enantiopurity (97% ee). The (R)-enantiomer can also be isolated in high enantiopurity. (See, WO 2003022785).

The optical activity of a compound can potentially be further enhanced through a direct crystallization (Li et al., *J. Pharm. Sci.* 86(10):1073 (1997)). The molecular chirality of a given compound is expressed in its overall crystallography, so it is sometimes possible to achieve an enantiomeric resolution spontaneously through the course of the crystallization. A crystalline solid is characterized by a high degree of internal order, consisting of a three-dimensional translational repetition of a basic structural pattern (Brittain, H. G. *Pharmaceutical Research*, 7(7), 683-690, 1990). Hence, it is also possible to reject other side-product impurities during the crystallization process. Disclosed in this invention is a detailed description of a crystallization process which serves to increase both the enantiopurity as well as the overall purity of the Formula I' compound.

The present invention is directed to the compounds according to Formula I' which demonstrate a protective effect against HIV infection by inhibiting the binding of HIV to the chemokine receptor CXCR4. The Formula I' compounds also display an anti-inflammatory effect, as shown in murine models, by inhibiting the binding of the natural chemokine SDF-1 to the chemokine receptor CXCR4. This invention, in particular, describes various methods for the synthesis and isolation of pure forms of the compounds as described below. The experimental procedures use the (S) enantiomer as an example, but the procedures are also valid for the (R) enantiomer or the (RS) racemate.

Schemes 5-8 illustrate the synthesis of a compound having Formula I. The same procedure may be utilized when making substituted derivatives of Formula I compounds (i.e., compounds having Formula I'). Accordingly, when a compound according to Formula "X" is exemplified below, the description also applies to the use of Formula "X'" compounds as well. Furthermore, it should be understood that the reaction conditions shown in Schemes 5-8 below are only exemplary, and can be further optimized by using alternative reagents and/or conditions based on well-known chemical principles and protocols, as well as the teachings herein.

Imine Formation

This invention provides a process for the efficient formation of an amino-substituted 5,6,7,8-tetrahydroquinoline of Formula II with an alkyl aldehyde of Formula III, as illustrated in Scheme 5.

Scheme 5

As a preliminary step, the amino-substituted 5,6,7,8-tetrahydroquinoline hydrochloride salt is treated with an aqueous base such as 10% sodium hydroxide and extracted with an organic solvent such as dichloromethane to isolate the amine freebase. In the preferred process, an optically active amine is used as a reagent (as depicted in Formula II), with the preferred isomer being the (S)-isomer.

Then, a stoichiometrically equal mixture of the 8-amino-5,6,7,8-tetrahydroquinoline amine freebase (Formula II) and the aldehyde (Formula III) are reacted in an organic solvent in the presence of an anhydrous inorganic salt. See, for example: Hamilton et al., *Tetrahedron Lett.*, 34:2847-2850 (1993) and Balenović et al., *J. Org. Chem.* 17:1459-1560 (1952). Exemplary organic solvents include, without limitation, diethyl ether, dimethylformamide, ethyl acetate, dichloromethane, chloroform, tetrahydrofuran, acetonitrile, ethylene glycol dimethyl ether, toluene and benzene with a preferred solvent being tetrahydrofuran.

Examples of inorganic salts include, but are not limited to, anhydrous magnesium sulfate, potassium carbonate, magnesium carbonate, sodium sulfate and sodium bicarbonate with a preferred inorganic salt being anhydrous potassium carbonate as shown in Scheme 5. Salt loading ranges from 0.5 to 2.0 stoichiometric equivalents, with 1.0 stoichiometric equivalent being preferred. Other dehydrating agents, such as molecular sieves, can also be used. In the case of toluene or benzene solvents, a Dean-Stark trap (filled with molecular sieves) can be employed in the reaction to remove water.

Reaction concentrations typically range from 0.05 M to 2.0 M with a preferred concentration of reagent II and III being in the 0.5 M range. The course of the reaction can be readily followed by $^1$H nuclear magnetic resonance (NMR) spectroscopy. Temperatures for the reaction are from −20° C. to reflux, with a preferred temperature being near ambient temperature, or 23° C.

The imine is typically isolated via filtration of the reaction mixture (to remove the inorganic salt) through a glass frit, filter paper or other form of filter. Generally, the conversion of the reaction is 95-100% (as measured by $^1$H NMR).

Imine Reduction

This invention provides a process for the chemical reduction of the imine (Formula IV) to the reduced form (Formula V), as illustrated in Scheme 6.

Examples of organic acids are formic acid, oxalic acid, citric acid, acetic acid and propionic acid, with acetic acid being the preferred reagent.

Reaction of the borohydride with the metal salt or organic acid is done in an organic solvent, examples of which include, but are not limited to, diethyl ether, dimethoxyethane, tetrahydrofuran, dichloromethane, benzene and toluene. A preferred solvent is tetrahydrofuran. The reaction is usually performed at a reduced temperature, typically between −40° C. and 0° C., with a preferred temperature being in the −25 to −5° C. range. Reaction yields range from 65-90%, with a typical yield for the zinc chloride/sodium borohydride method being approximately 80%.

Alkylation Process

This invention provides a process for the alkylation of the secondary amine (Formula V) with an amine-protected 2-chloromethylbenzimidazole (Formula VI) to synthesize the tertiary amine according to Formula VII. More particularly, Scheme 7 depicts the reaction of the secondary amine (Formula V) with the amine-protected 2-chloromethylbenzimidazole (Formula VI) in an organic solvent at elevated temperature in the presence of an amine base and a catalytic amount of an iodide. (See also, Cook et al., *Tetrahedron*, 54:3999-4012 (1998)).

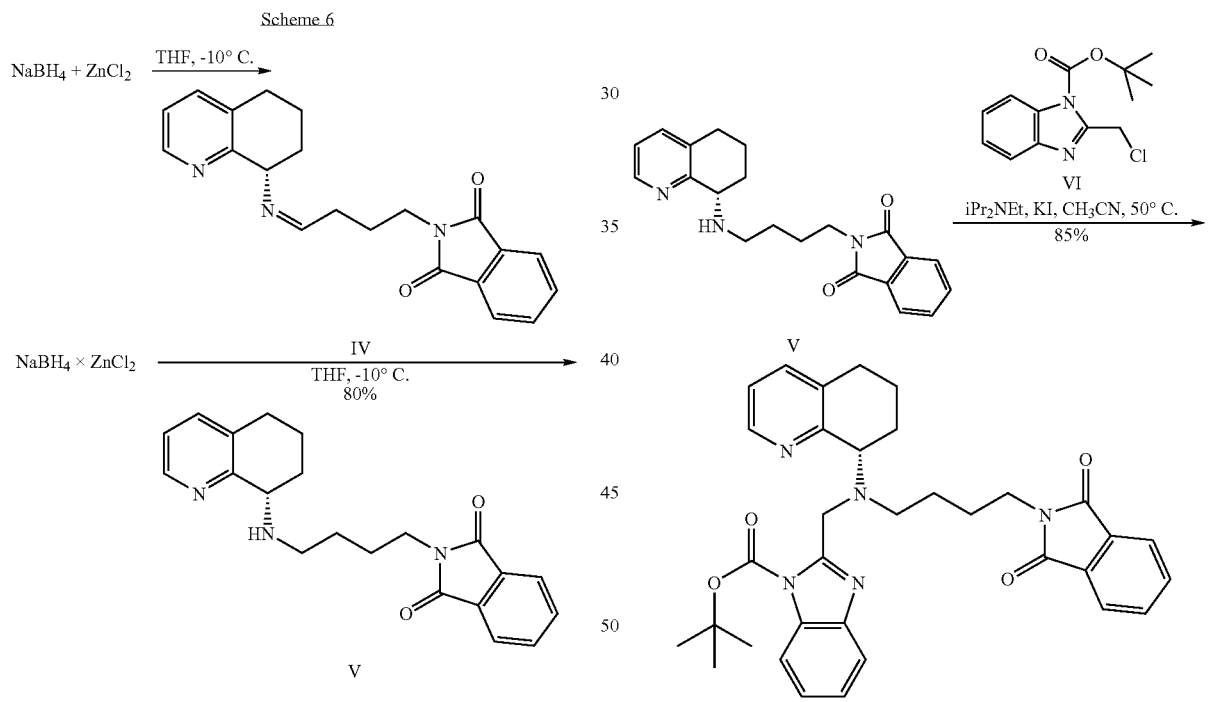

As shown, a metal hydride reducing agent is reacted with a metal salt or an organic acid in an organic solvent to generate a reducing agent. Then, the imine solution is added to the reducing agent, which leads to the reduction of the imine.

Examples of metal hydride reducing agents are sodium borohydride, lithium aluminum hydride, sodium triacetoxyborohydride, sodium cyanoborohydride and lithium borohydride with the preferred reagent being sodium borohydride.

Examples of metal salts are zinc chloride, potassium hydroxide, sodium hydroxide and sodium acetate, with zinc chloride being the preferred reagent.

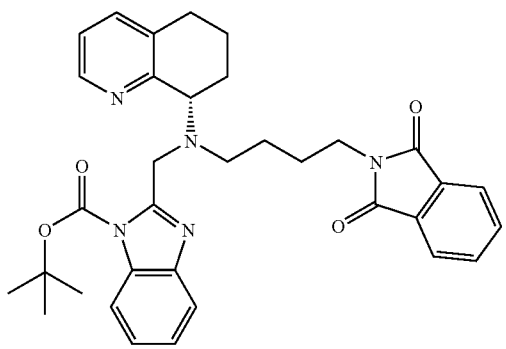

VII

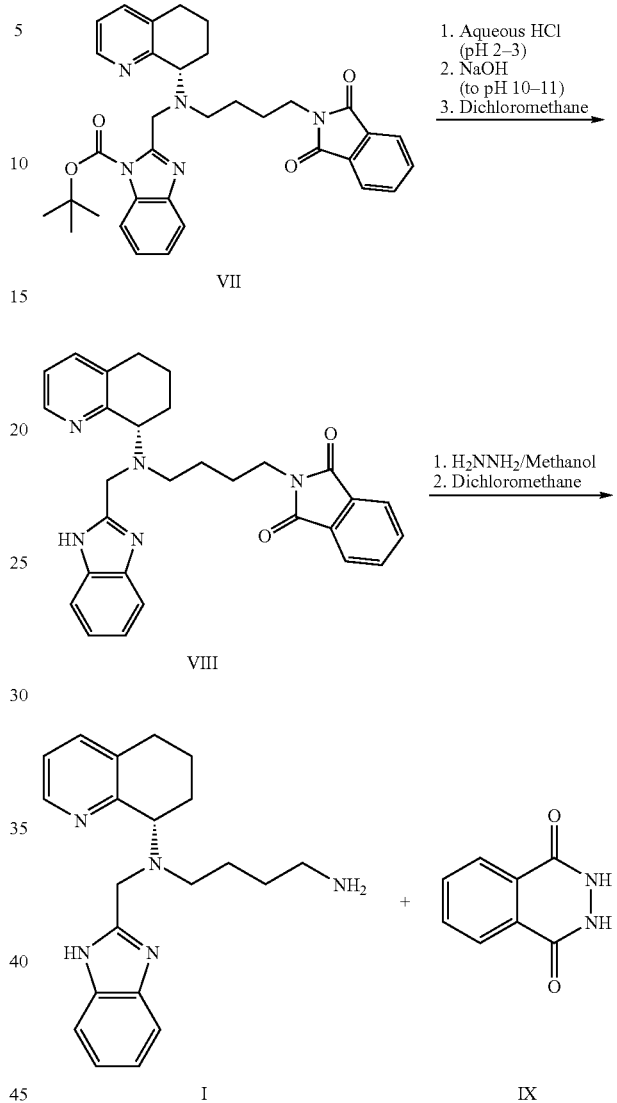

As shown, the Formula VI compound bears a butoxycarbonyl amine protecting group. It should be readily apparent that other amine protecting groups are also useful in the practice of the present invention and could be easily substituted for the butoxycarbonyl group and thereafter removed using known methods. Examples of other protecting groups include, but are not limited to, methoxycarbonyl, benzyl, benzyloxycarbonyl, allyl, toluenesulfonyl, methanesulfonyl, and acetyl.

The reaction is typically carried out with a stoichiometric excess of the Formula VI compound. In particular, the reaction is generally carried out with 1.0 to 2.0 equivalents of the Formula VI compound (compared to the Formula V compound) with a preferred range being 1.05-1.15 equivalents.

A number of amine bases have been used in the reaction, including but not limited to, triethylamine and diisopropylethylamine, with the preferred reagent being diisopropylethylamine. Other amines which are applicable include tetramethylguanidine, 1,8-diazabicyclo[5.4.0]undec-7-ene and 1,4-diazabicyclo[2.2.2]octane. Typically, 1.1 to 1.5 equivalents of the amine base relative to the amine V are used.

Solvents for the reaction include dichloromethane, chloroform, tetrahydrofuran, dimethylformamide, benzene, toluene and acetonitrile with acetonitrile being a preferred solvent. Reaction temperatures range from ambient to reflux, with an ideal range being 50-60° C.

A catalytic amount (0.01 to 0.2 equivalents) of an iodide source, such as potassium iodide, cesium iodide, sodium iodide or tetrabutylammonium iodide is typically added to increase the reaction rate. The typical yield of the Formula VII compound for the reaction is 80-95%.

Amine Protecting Group Removal

Furthermore, this invention provides procedures for the removal of the butoxycarbonyl protecting group, if present, and the phthalimide amine protecting groups from the Formula VII compound. Scheme 8 illustrates the procedures for deprotection.

In a preferred embodiment, the benzimidazole amine t-butoxycarbonyl protecting group is selectively hydrolyzed under acidic aqueous conditions to generate the Formula VIII compound. Subsequently, the primary amine phthalimide protecting group of the Formula VIII compound is then hydrolyzed in an organic solvent with hydrazine or another amine-based reagent. Thereafter, the deprotected compound according to Formula I, which is free of hydrazine and other side products, including hydrazide IX, can be isolated.

The removal of the butoxycarbonyl protecting group from the Formula VII compound can be accomplished under standard conditions using aqueous acidic media. A number of acids can be employed, such as hydrochloric acid, sulfuric acid, acetic acid, trifluoroacetic acid, 4-toluenesulfonic acid, methanesulfonic acid and propionic acid. A preferred condition is aqueous hydrochloric acid (pH 2-3). The conversion to the Formula VIII compound is very efficient, typically 95% yield or more. Upon completion of the reaction, which typically takes 12-16 hours and can be monitored by HPLC, the pH of the solution is raised through the addition of a base such as 10% aqueous sodium hydroxide to about a pH of 10-12, and the mixture is extracted into an organic solvent such as dichloromethane.

The removal of the phthalimide protecting group from the Formula VIII compound can be accomplished under standard conditions using a number of different reagents including, but not limited to ammonia, methylamine, butylamine, ethylenediamine, hydrazine hydrate and sodium borohydride followed by acetic acid. A preferred reagent is hydrazine hydrate. Typically, about 8-10 equivalents of hydrazine hydrate are used. Solvents for the reaction include methanol, ethanol, isopropanol, ethylene glycol, dimethylformamide and tetrahydrofuran. The reaction is carried out at ambient temperature or at elevated temperature (reflux), at 50-100 C, solvent dependant. Generally, the reaction times are on the order of 12-24 hours at ambient temperature. Removal of the hydrazide side product (i.e., the Formula IX compound) can be accomplished through filtration. The filtration of the hydrazide side product can be made more efficient through the addition of an organic solvent such as dichloromethane to the reaction mixture to aid in the complete precipitation of the Formula IX compound from solution.

Although sequential removal of the amine protecting groups is exemplified, it should be apparent to one of skill in the art that a benzimidazole amine protecting group can be selected which can be removed simultaneously with the phalamide amine protecting group.

Optional Decolorizing and Purification Procedures:

This invention also provides optional additional steps for the purification and/or decolorization of the Formula I compound as follows. In one example, an aqueous solution of the compound having Formula I may be treated with decolorizing carbon to remove colored impurities. In another example, the compound having Formula I may be extracted using an organic solvent, and purified using silica gel flash chromatography.

The Formula I compound in freebase form, in a mixture of dichloromethane and another solvent can be washed with an aqueous base such as 0.5N sodium hydroxide to remove traces of hydrazine. The Formula I compound can then be extracted into a dilute aqueous acid such as 1N hydrochloroic acid. The Formula I compound is readily soluble in aqueous media at a pH at or below 6.0. If the pH of the aqueous solution is below 5, it can then be adjusted to 5-7, with a preferred pH being 6.0 for the removal of impurities. Non-polar organic impurities will remain in the organic layer. A number of solvents can be used, if desired, for further extraction of non-polar organic impurities including ethyl acetate, methyl t-butyl ether, tetrahydrofuran, dichloromethane and chloroform.

If a decolorizing procedure is desired, activated charcoal can be added to the aqueous solution. Typically, 10 to 30 weight % carbon is used (relative to the amount of compound I), and the mixture is stirred for 3-16 hours. A typical procedure uses 20 weight % activated carbon in pH 6 aqueous for 8 hours. The mixture is then filtered to remove the carbon. A number of alternative varieties of activated carbon can be used, including, but not limited to Darco® G-60, Darco® KB or Norit® (registered trademark of Norit Americas Inc. Marshall, Tex.).

Alternatively, the decolorizing carbon treatment can be applied to the filtered reaction mixture comprising compound I, after the washes with aqueous base and prior to extraction into aqueous acid. Solubilization of the Formula I compound in other organic solvents, such as methanol, ethanol or isopropanol, followed by decolorizing carbon treatment can alternatively be conducted.

In order to extract the Formula I compound into organic media, the pH of the aqueous solution can be increased to about 11-12 through the addition of an aqueous base, such as 10% sodium hydroxide. The freebase Formula I compound can then be extracted into an organic solvent such as dichloromethane, chloroform or toluene, with dichloromethane being a preferred solvent.

If desired, the solution can be passed through a column, which has been pre-treated with an organic solvent mixture. The column can consist of florisil, silica gel or alumina, with silica gel being a preferred solid phase. Typically, 0.5 to 10 weight equivalents of silica gel (relative to compound I) are employed in the purification, with 0.5-2.0 weight equivalents being preferred. Typically, 240-400 mesh, 60 Å column chromatography grade silica gel is used. The elution of the compound can be achieved in fractions, by using a mixture of alcohol and chlorinated organic solvents such as methanol and dichloromethane. In one example, the eluent is a mixture of 79% dichloromethane, 20% methanol and 1% concentrated aqueous ammonium hydroxide (by volume). The elution can be followed by sampling the eluted fractions, and analyzing by thin layer chromatography, using procedures that would be familiar to those with skill in the art.

Following the silica gel column, the combined fractions containing compound I in organic media are typically washed once with a dilute inorganic base such as 1 N sodium hydroxide to ensure that the material is completely freebased. Following the wash, the organic fractions are dried with an anhydrous desiccant such as anhydrous magnesium sulfate or anhydrous sodium sulfate.

Optional Crystallization

For synthetic routes initiated with an optically active Formula II compound, and therefore providing an optically active Formula I compound, this invention provides a process for the crystallization of the Formula I compound from a mixture of organic solvents. In one example, the invention provides a process for making an optically active compound having Formula I, comprising:

a) concentrating a solution containing a compound having Formula I in a mixture of organic solvents (solvent A), to form a solution with a predetermined concentration;

b) adding a suitable crystallization solvent or mixture of solvents (solvent B) to the solution in a), and optional removal of the residual solvent A by a co-distillation process to a predetermined volume or concentration at a specified temperature;

c) seeding the solution in b) at an appropriate temperature with a small amount of pure crystalline Formula I compound (of the appropriate enantiomeric form), and cooling the mixture with agitation under controlled conditions such that crystals having Formula I are spontaneously formed; and d) filtering and drying crystalline material.

The concentration of the Formula I compound solution is generally conducted under vacuum, where the primary solvent A can be easily and quickly removed to a predetermined volume, typically about 500 mg/mL. If desired, the solution can be concentrated to dryness. In one example, solvent A comprises dichloromethane. A typical residual dichloromethane level if the mixture is concentrated to dryness, under approximately 25 mmHg vacuum, would be on the order of 30 mole % relative to the Formula I compound.

A crystallization solvent (solvent B) is then added which can include, but is not limited to the following, or mixtures of the following: tetrahydrofuran, ethyl acetate, cumene, isopropyl acetate, n-propyl acetate, dichloromethane, ethanol, isopropanol, methanol, isopropyl ether, diethyl ether and t-butyl methyl ether. A preferred solvent is isopropyl acetate. A sufficient volume of solvent B is added to typically reach a complete solvation of compound I at an elevated temperature. The elevated temperature will depend on the nature of the solvent, with a reflux condition being the highest temperature possible. As an example, in the case of isopropyl acetate, it is possible to achieve complete solubility with concentration of compound I of approximately 125 mg/mL at a temperature of 60-65° C.

At this point, if desired, the solution can be placed under vacuum, and concentrated. During the concentration process, which can be conducted at ambient or elevated temperatures, the level of solvent A in the solution can be monitored by $^1$H NMR measurements. The concentration of solvent A can therefore be controlled during the co-distillation process. In the case of dichloromethane (solvent A) in isopropyl acetate (solvent B), a level of less than 2 mol % of solvent A is preferred.

The concentration is then typically carried out to a predetermined final concentration, at which point the Formula I compound is saturated or supersaturated. In the case of isopropyl acetate, a concentration of between 100 and 200 mg/mL is used, with 125 mg/mL being a preferable level. At this point, the mixture is allowed to cool, with agitation. Generally, a small amount of crystalline Formula I compound is added to the solution to "seed" the crystallization process. The crystals will spontaneously begin to form upon cooling. Isolation of the crystalline material is possible through filtration.

The yield of crystalline material depends on the solvent mixtures used. For a concentration of 125 mg/mL of the Formula I compound in isopropyl acetate, the yield of crystalline material is typically 75%, and is isolated as a fine white to pale yellow powder. In order to reduce the levels of residual solvents on or in the crystalline material, the crystalline Formula I compound is typically dried in a 40° C. vacuum oven (2-5 mmHg vacuum) for 24 hours or more.

The following examples are intended to illustrate, but not to limit, the invention.

EXAMPLE 1

Synthesis of (N'-(1H-benzimidazol-2-ylmethyl)-N'-5,6,7,8-tetrahydroquinolin-8-yl-1,4-butanediamine from a Phthalimide-Substituted Alkyl Aldehyde Preparation of (S)-8-amino-5,6,7,8-tetrahydroquinoline freebase (II) from amine Salt

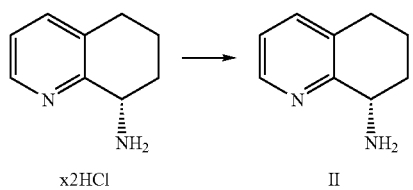

(S)-8-amino-5,6,7,8-tetrahydroquinoline hydrochloride (23.4 kg, 106 mol) was dissolved in deionized water (60 L) and neutralized to pH 7 with a 50% sodium hydroxide solution (~11.5 kg). The mixture was extracted with dichloromethane (126 kg). The pH of the aqueous layer was re-adjusted to 7 with 50% NaOH, and was extracted again with dichloromethane (126 kg). The dichloromethane fractions are then discarded. The pH of the aqueous layer was increased to 13 with 50% NaOH. The aqueous layer was then extracted with dichloromethane (2×126 kg). The combined organic layers were dried (sodium sulfate) and concentrated in vacuo to afford (S)-8-amino-5,6,7,8-tetrahydroquinoline (12.7 kg, 81% yield, purity: 96% by HPLC) as a dark brown oil. $^1$H NMR (CDCl$_3$) δ 1.64-1.84 (m, 2H), 1.94-2.01 (m, 1H), 2.14-2.23 (m, 1H), 2.69-2.87 (m, 2H), 3.99 (dd, 1H, J=7.7, 5.3 Hz), 7.06 (dd, 1H, J=7.7, 4.4 Hz), 7.36 (d, 1H, J=7.5 Hz), 8.41 (d, 1H, J=4.4 Hz).

Chiral purity determined by gas chromatography to be 97.5% ee (separated by chiral GC, J&W CycloSil B column, isothermally run at 130° C. for 40 min., (S)-(+)-enantiomer$_{rt}$=26.3 min, (R)-(−)-enantiomer$_{rt}$=28.7 min).

Imine Formation (IV) with K$_2$CO$_3$ in THF:

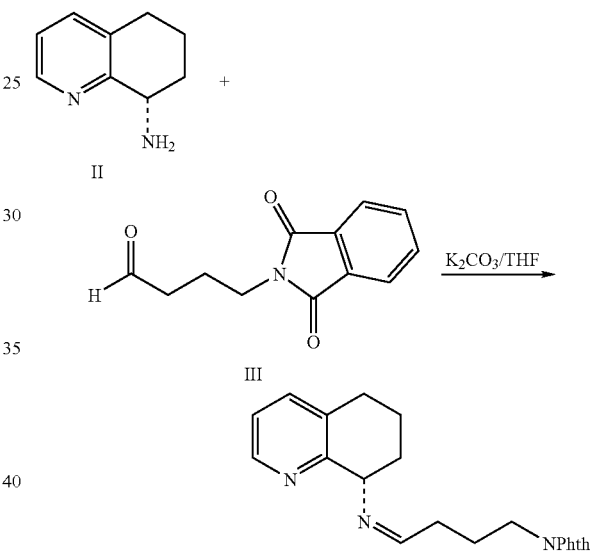

To a solution of 8-amino-5,6,7,8-tetrahydroquinoline (12.7 kg, 85.8 mmol, 1.0 eq.) in THF (50 L) was added 4-(1,3-dioxo-1,3-dihydroisoindol-2-yl)butan-1-al (15.8 kg, 72.8 mmol, 0.8 eq) and 325 mesh potassium carbonate (11.8 kg, 85.8 mol, 1.0 eq). The mixture was then stirred for 2 hours. A proton NMR of an aliquot from the sample was used to determine stoichiometry. Based on the calculation, another 0.18 eq of aldehyde (15.4 mol, 3.35 kg) was added. After stirring for 2 hours, a second proton NMR aliquot showed complete and clean imine IV formation (>97% conversion). $^1$H NMR (CDCl$_3$) δ 1.76-2.19 (series of m, 6H), 2.35 (m, 2H), 2.78 (m, 2H), 3.73 (m, 2H), 4.31 (t, 1H, J=5.1 Hz), 7.05 (dd, 1H, J=7.8, 4.8 Hz), 7.38 (d, 1H, J=7.8 Hz), 7.69 (m, 2H), 7.80 (m, 2H), 7.82 (t, 1H, J=4.1 Hz), 8.38 (d, 1H, J=4.8 Hz). The mixture was then filtered.

Generally, sometrically equal amount of the amine II and the aldehyde III are used in the imine formations, with an equimolar amount of dehydrating agent (if used). Alternatively, imines may be formed without a dehydrating agent using THF, dichloromethane, or methanol. Imines may also be formed using dimethoxyethane or diethyl ether as the solvent and $K_2CO_3$ as the dehydrating agent. Alternatively, imines may be formed using dichloromethane as the solvent and $MgSO_4$ as the dehydrating agent. These alternative conditions for forming imines gave a >80% conversion to the imine as measured by NMR.

Reduction of Imine Using Acetic Acid/Sodium Borohydride

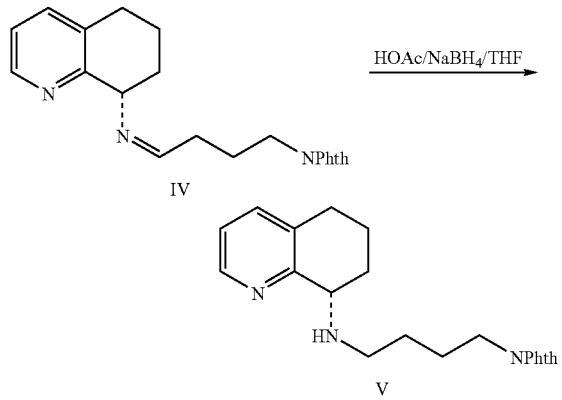

Reagent formation: To a mechanically stirred −20° C. (internal temperature) suspension of powdered sodium borohydride (15.3 g, 400 mmol, 1.2 eq.) in THF (1700 mL) in a 5 L flask was added glacial acetic acid (36.2 mL, 633 mmol, 1.9 eq.) in a dropwise manner over 15 minutes. An effervescence occurred upon addition, which subsided after approximately 5-10 minutes following the completion of addition. The mixture was then stirred until it became homogeneous and translucent (60 minutes), and was then cooled to −20° C.

The filtered imine IV (338 mmol in 1.7 L THF) was then cooled to −20° C. (internal temperature), and was added over 15 minutes to the −20° C. borohydride mixture via cannula. Following addition, the reaction was stirred, at a temperature of between −15 and −20° C. Aliquots of the reaction mixture were taken at 15 minute intervals, starting at a stirring time of 30 minutes. The reaction was determined to be complete at 75 minutes stirring time, as measured by proton NMR.

Work-up procedures involve quenching the reaction, removing impurities, and recovering the product. The reaction was quenched with saturated aqueous sodium bicarbonate at −20° C. (700 mL), and was allowed to warm for 15 minutes. Dichloromethane (3 L) was then added and the aqueous and organic layers were separated. The organic layer was extracted two more times with dichloromethane (1.5 L fractions). If the sodium bicarbonate precipitates upon addition to the reaction (after warming), sufficient distilled water is added to ensure homogeneity of the aqueous layer. In this example, 300 mL water was added.

To remove impurities, the combined dichloromethane fractions are concentrated, and the residue is taken up in 5% aqueous acetic acid (1.2 L). The aqueous layer is washed once with hexanes (1.5 L). The hexanes layer is washed with a small amount of water. The combined aqueous fractions are then washed twice with methyl t-butyl ether (2×600 mL fractions). Separation of aqueous and organic layers during the MTBE extractions may take 10-15 minutes. Generally, the more complete the separation, the more efficient the impurity removal process will be.

To recover the product, solid sodium bicarbonate is slowly added to the well-stirred aqueous layer to bring the pH to 7 (measured by pH paper). If there is still a residual amount of MTBE remaining, it is separated at this stage from the aqueous layer. The aqueous layer is extracted three times with dichloromethane (3×1 L fractions). The combined dichloromethane fractions were then washed with saturated aqueous sodium bicarbonate (300 mL—to remove residual acetic acid), separated, dried over anhydrous magnesium sulfate, filtered and concentrated to afford the desired product, which was isolated as a pale foam in a yield of 92.3 g (74%). $^1$H NMR (CDCl$_3$) δ 1.59-2.17 (series of m, 8H), 2.74 (m, 4H), 3.72 (t, 2H, J=7.2 Hz), 3.72 (m, 1H), 7.04 (dd, 1H, J=7.8, 4.8 Hz), 7.35 (dd, 1H, J=7.8, 0.6 Hz), 7.70 (m, 2H), 7.82 (m, 2H), 8.36 (dd, 1H, J=4.8, 0.6 Hz). ES-MS m/z 350 (M+H); Purity by HPLC: 90.9%. Chiral purity 97% ee (by chiral HPLC).

Reduction of Imine Using Zinc Chloride/Sodium Borohydride:

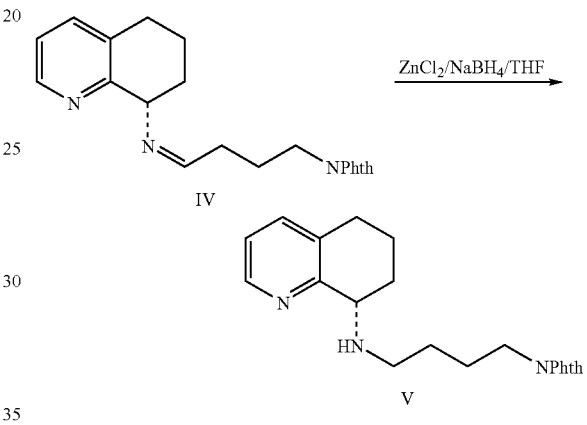

First, the reducing agent is formed, followed by reduction of the imine, and work-up. To a reactor containing THF (80 L) was added zinc (II) chloride (12.8 kg, 94.3 mol). A mild exothermic occurs upon dissolution. Sodium borohydride (3.24 kg, 85.8 mol) is then added slowly. The mixture is then stirred for one hour, during which time a homogeneous solution is formed. The solution is then cooled to −15° C.

A solution of imine IV (85.8 mmol) in THF (50 L) was cooled to −20° C., and was added slowly to the cooled solution of zinc chloride and sodium borohydride, maintaining the internal temperature of the reaction flask between −7 and −15° C. The reaction was then stirred at −15° C. for 3 hours. At this point, an in-process HPLC determined that the reaction was complete.

For work-up, a solution of 6N aqueous HCl (35 L) was slowly added, maintaining the temperature below −5° C., until the pH of the aqueous layer measured 2-3. The reaction was allowed to warm to room temperature, then a solution of 13% aqueous sodium carbonate (12 L) was added until the pH reached 4. The reactor was placed under vacuum, and the THF solvent was removed by distillation. Water (120 L) and dichloromethane (160 L) were then added. The mixture was then agitated, and then the aqueous and organic layers were separated. The organic layer was then washed with concentrated aqueous ammonium hydroxide (100 L) and then water (60 L). The dichloromethane solution was then passed through a 20 kg pad of silica gel. The dichloromethane solution was then concentrated under vacuum, then diisopropyl ether (50 L) was added. The solution was then concentrated under vacuum, and was then cooled slowly to −10° C., with agitation, during which time, a precipitate formed. The precipitate (desired amine V) was filtered, and washed with diisopropyl ether. After drying under vacuum, the desired product V was obtained in a 20.4 kg yield (65%, corrected for solvent and purity) as a light brown crystalline solid. Purity by HPLC 95%.

Alkylation with Carbamate Cleavage in Work-up

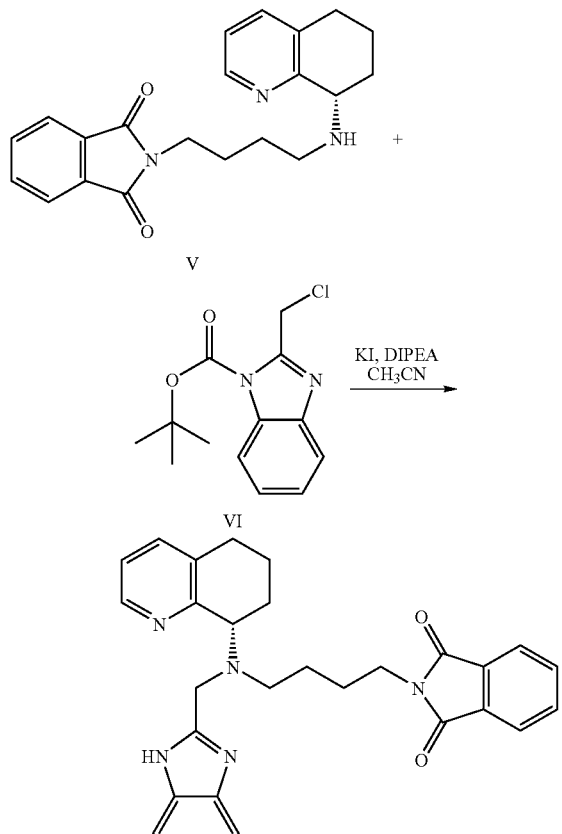

To a reactor was charged amine V (9.9 kg, 28.6 mol), benzimidazole VI (8.0 kg, 30.0 mol) and potassium iodide (144 g, 0.86 mol). A solution of diisopropylethylamine (6.0 L, 34.3 mol) in anhydrous acetonitrile (60 L) was then added. The mixture was stirred, and the flask was warmed to a 50° C. internal temperature. The temperature was maintained for 200 minutes, at which point, an NMR aliquot determined that the reaction was complete. The reaction was then cooled, and the solvent was removed under vacuum (25 mmHg). The residue was then suspended in water (50 L), and 4N aqueous HCl (~15 L) was added slowly until a pH of 2 was reached. The aqueous layer was then extracted twice times with 40 L portions of methyl t-butyl ether (which were discarded). The aqueous layer was then stirred for 16 hours at ambient temperature. Toluene (60 L) was then added, and a 3N aqueous NaOH solution was added until the pH of the aqueous layer reached 11. The layers were then separated. The organic layer was then dried over anhydrous sodium sulfate. The solution was then filtered and stored at 3° C. or below as a stock solution. An aliquot of the solution was concentrated, and the purity of the product VIII was determined to be 91% by HPLC. The yield was determined, by concentration of a representative aliquot to dryness, to be 83% (11.3 kg of VIII in the stock solution). $^1$H NMR (CDCl$_3$) δ 1.20-1.50 (m, 2H), 1.60-1.80 (m, 1H), 1.85-2.10 (m, 2H), 2.45-2.65 (m, 3H), 2.65-2.95 (m, 3H), 4.00 (d, 1H, J=16.8 Hz), 4.07 (m, 1H), 4.12 (d, 1H, J=16.8 Hz), 7.10-7.30 (m, 4H), 7.42 (d, 1H, J=7.5 Hz), 7.55 (br s, 1H), 8.59 (d, 1H, J=4.4 Hz). ES-MS m/z 480 (M+H).

Phthalimide Deprotection with Decolorizing Treatment and Selective Extraction of I

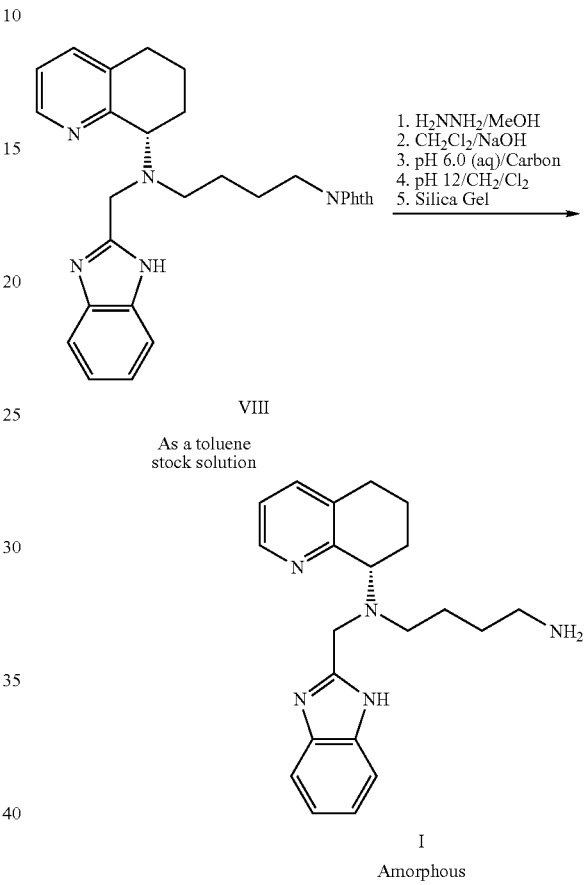

The toluene stock solution of VIII (94 kg, containing 11.3 kg of VIII, 23.9 mol, corrected for purity) was concentrated under reduced pressure to remove most of the toluene. The oily residue was dissolved in methanol (25 L) and hydrazine hydrate (14 kg, ~230 mol (N$_2$H$_4$.1.5H$_2$O)) was then added. The solution was stirred mechanically at room temperature for 17 h. The phthalylhydrazide was removed by filtration and the filtrate was concentrated under reduced pressure. Dichloromethane (20 L) was added and the solution was washed with a 0.5N NaOH solution (2×30 L). The organic and aqueous phases were separated and water (20 L) was then added. 3N HCl was then added to bring the pH to 5-6. The aqueous and organic phases were separated, and the aqueous phase was treated with activated carbon (Norit G-60, 3 kg) for 16 h. The mixture was filtered and the pH of the filtrate was adjusted to 12 with 3N NaOH. The resulting solution was extracted with dichloromethane (50 L). The pH of the aqueous phase was re-adjusted to 12 with 3N NaOH and was extracted with a second portion of dichloromethane (50 L).

The combined organic fractions were loaded on to a silica gel column (12 kg) and the product was then eluted using a 79:20:1 dichloromethane/methanol/ammonium hydroxide solution. In this example, the silica gel was pre-conditioned with the eluent prior to loading the compound. A series of 50 L fractions were collected, and analyzed by TLC. The pure fractions were collected (3 fractions) and the total volume was concentrated to 20 L. The residue was dissolved in dichloromethane (60 L) and washed with 1.25 N NaOH (30 L). The organic phase was then dried with anhydrous $Na_2SO_4$ and filtered to afford compound I (N'-(1H-benzimidazol-2-ylmethyl)-N'-(5,6,7,8-tetrahydro-quinolin-8-yl)-butane-1,4-diamine) as a dichloromethane solution (4.5 kg, 56%, 98% pure by HPLC, 98% e.e.). $^1$H NMR ($CDCl_3$) δ 1.23-1.49 (m, 4H), 1.62-1.77 (m, 1H), 1.85-1.97 (m, 1H), 2.00-2.10 (m, 1H), 2.16-2.26 (m, 1H), 2.51 (t, 2H, J=6.8 Hz), 2.54-2.62 (m, 1H), 2.67-2.78 (m, 1H), 2.81-2.92 (m, 1H), 7.15 (d, 1H, J=7.6 Hz), 7.18-7.23 (m, 2H), 7.59 (br s, 1H), 8.60 (d, 1H, J=4.4 Hz). ES-MS m/z 350 (M+H).

Crystallization of Compound I

Compound I may be crystallized as a free base using isopropyl acetate solvent, with co-distillation removal of dichloromethane. A solution of I (4.5 kg, 12.9 mol) in $CH_2Cl_2$ (50 L) was stirred with anhydrous $Na_2SO_4$ (500 g, 3.5 mol) for 8 hours at room temperature. The mixture was filtered and transferred into a reactor and the solution was placed under an atmosphere of nitrogen. The mixture was warmed to 25° C. and placed under vacuum (approximately 30 mmHg) to remove the $CH_2Cl_2$, maintaining the temperature of the solution between 20° C. and 30° C. during the concentration. Isopropyl acetate (32 L) was then added.

A proton NMR aliquot showed a dichloromethane content of ~9 mol % relative to isopropyl acetate. The mixture was placed under vacuum again, and was concentrated to a volume of ~15 L, maintaining an internal temperature of less than 40° C. A second portion of isopropyl acetate (17 L) was added and the solution was concentrated to ~15 L, keeping the internal temperature between 30 and 40° C. An aliquot of the solution showed a residual dichloromethane level (relative to isopropyl acetate) to be less than 1 mol % by $^1$H NMR.

The vacuum was then released, and the mixture was placed under a nitrogen atmosphere, and was heated to 65° C. At this point, the material was soluble, and was allowed to cool to 50° C., at which point, 100 g of crystalline I was added. The solution was allowed to cool slowly to room temperature (over 8 h) with stirring. During this time, crystals of compound I formed as a fine, off-white powder. The mixture was filtered through a fritted glass funnel (with vacuum) and the solids were washed with cold (~5° C.) isopropyl acetate (100 mL). The crystals were dried under vacuum (2 mm Hg, 40° C.) for 24 h to afford I as a fine off-white powder (3.0 kg, 67%). Achiral purity: 99% (HPLC). Chiral Purity: >99% ee. Residual solvents (GC) Isopropyl Acetate, 3700 ppm; dichloromethane, 31 ppm.

In an alternative crystallization procedure, compound I (1.1 kg) was transferred to a 20 L flask, to which isopropyl acetate (10 L) was added. The flask was heated slowly to an internal temperature of 67° C., at which point all the solids had dissolved and the resulting solution was transparent. The solution was then cooled slowly to 50° C., with agitation, and was seeded with 10 g of crystalline compound I. The mixture was then cooled to ambient temperature with agitation, during which time the compound I precipitated as fine crystals. The flask was cooled to 0° C., and the slurry was filtered, washing with 0° C. isopropyl acetate (1 L). The crystalline compound I was then dried in a 40° C. vacuum oven (27 mm Hg) for 24 hours to give 820 g (75%) yield of crystalline material.

The crystalline compound I may also be isolated from a number of different solvent systems. Compound I is soluble at >600 mg/mL in 55° C. tetrahydrofuran, and can be recovered as crystalline material by cooling the solution. Similarly, compound I can be isolated as crystalline material from a hot solution of cumene. Compound I is very soluble in dichloromethane (>700 mg/mL), but can be precipitated as a crystalline material from the solution through the addition of diethyl ether. Ethyl acetate is an effective solvent for crystallization, with solubilities of compound I of ca. 150 mg/mL at 60° C. being achievable.

EXAMPLE 2

Synthesis of (N'-(1H-benzimidazol-2-ylmethyl)-N'-5,6,7,8-tetrahydroquinolin-8-yl-1,4-butanediamine from a tert-butoxycarbonyl (BOC) substituted alkyl aldehyde Preparation of
N,N-Di-tert-butoxycarbonylaminobutyraldehyde
Synthesis (Formula IIIa)

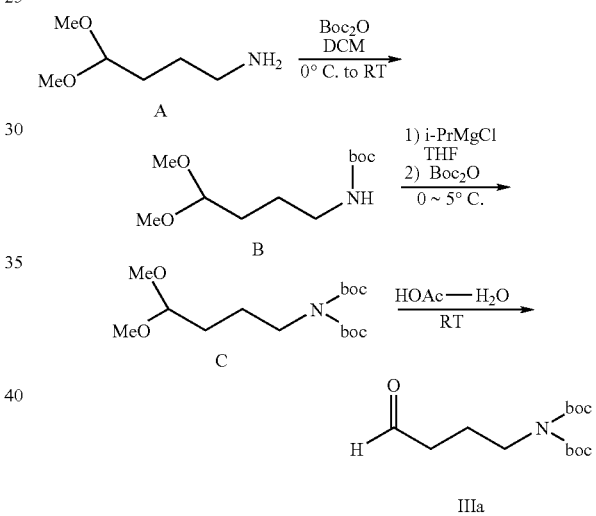

Aminoacetal A (133.19 g, 1.0 mol) was dissolved in dichloromethane (300 mL) and cooled in an ice-water bath. When internal temperature had dropped below 2° C., a solution of $Boc_2O$ (218.25 g, 1 eq.) in dichloromethane (200 mL) was added via a pressure-equalizing dropping funnel. The addition was kept at such a rate that the internal temperature remained below 10° C. After the addition, the cold bath was removed and the mixture was stirred at room temperature for 30 min. An aliquot was removed via a syringe and dried under high vacuum. NMR of the residue indicated completed and clean reaction. All volatiles were removed by rotary evaporation and the residue was further dried on high vacuum for 1 hour at 50° C. with stirring to give tert-butylcarbonylbutyraldehyde dimethyl acetal B in quantitative yield. $^1$H NMR (δ, $CDCl_3$): 4.61 (s, br, 1 H), 4.37 (t, J=5.4 Hz, 1 H), 3.32 (s, 6 H), 3.19-3.07 (m, 2 H), 1.68-1.50 (m, 4 H), 1.44 (s, 9 H) ppm.

Compound B from the above reaction was dissolved in anhydrous THF (700 mL) and cooled in an ice-water bath. When the internal temperature was below 4° C., i-PrMgCl (2.0 M in THF, 550 mL, 1.1 eq.) was added slowly via a pressure equalizing dropping funnel at a rate that kept the temperature at 5±2° C. The dropping funnel was rinsed with ~50 mL THF. The mixture was stirred in the cold bath for 20 min after the Grignard addition, and then a solution of Boc₂O (218.25 g, 1 eq.) in THF (200 mL) was added slowly that kept the temperature at 5±2° C. After 30 minutes, TLC and NMR confirmed clean and complete reaction. The reaction was quenched cold by drop-wise addition of aqueous HCl (6 M, 150 mL). Celite (66 g) and anhydrous MgSO₄ (67 g) were added. The mixture was stirred for 5 minutes and then filtered through a celite pad (1 cm celite on a 600 mL sintered glass funnel). The filtrate was concentrated to dryness to give di-tert-butylcarbonylbutyraldehyde dimethyl acetal C in quantitative yield. $^1$H NMR ($\delta$, CDCl₃): 4.37 (t, J=5.2 Hz, 1 H), 3.58 (t, J=7.01 Hz, 2 H), 3.31 (s, 6 H), 1.65-1.59 (m, 4 H), 1.50 (s, 18 H) ppm.

Crude C from above (~1 mol) was dissolved in THF (400 mL) and the solution was added to a mixture of HOAc (glacial, 1.5 L) and water (0.9 L). The mixture was stirred at room temperature for 24 h. All volatiles were removed by rotary evaporation under high vacuum (bath 45 ° C.), and the residue was partitioned between water (600 mL) and hexane (400 mL) at room temperature. The pH of the aqueous layer was adjusted to ≧10 by 4M NaOH while cooled in a cold-water bath (total 370 mL added). The aqueous was extracted with hexane (500 mL×2); the combined organic layers were washed once with saturated NaHCO₃ (600 mL) and dried with anhydrous MgSO₄ (100 g). The mixture was filtered through a silica pad (2 cm silica on a 600 mL sintered glass funnel) and the filter cake was rinsed with 200 mL of 4:1 hexane-ether. The filtrate was concentrated by rotary evaporation and further dried under high vacuum with stirring for 1 h to give di-tert-butylcarbonylbutyraldehyde (IIIa) as light yellow oil (222.44 g, 77.5% over 3 steps, 93% LC purity and 0.064% water content). $^1$H NMR ($\delta$, CDCl₃): 9.78 (t, J=1.4, 1 H), 3.62 (t, J=7.1 Hz, 2 H), 2.47 (td, $J_1$=7.4 Hz, $J_2$=1.2 Hz, 2 H), 1.91 (quent., J=7.29 Hz, 2 H), 1.51 (s, 18 H) ppm; MS (M/z): 310, 210.

Reductive Amination

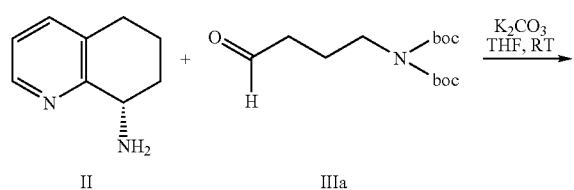

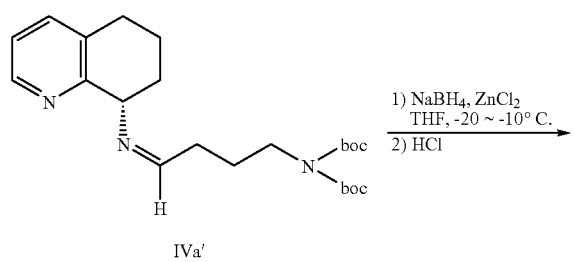

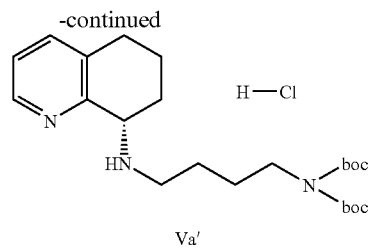

A 2 L, 3-neck round bottom flask was fitted with a mechanical stirrer, a thermometer, and a pressure-equalizing dropping funnel. (S)-8-amino-5,6,7,8-tetrahydroquinoline (II) (120.61 g, 0.81 mol) was dissolved in THF (400 mL) under N₂. Anhydrous K₂CO₃ (110 g, 0.80 mol) was added and the mixture was cooled in an ice-water bath. Di-tert-butylcarbonylbutyraldehyde (IIIa) (247.74 g, 0.80 mol) was dissolved in THF (200 mL) and added to the reaction mixture via the dropping funnel at such a rate to maintain the internal temperature below 5° C. The dropping funnel was rinsed with THF (100 mL in 2 portions). The cold bath was removed and the mixture was allowed to stir at room temperature until an aliquot NMR indicated complete imine formation. To avoid false completion results, a drop of reaction mixture was diluted with CDCl₃, and NMR was taken directly. Furthermore, the integration of $\delta$ 8.39 peak was calibrated to 1, so the aldehyde ($\delta$ 9.77, s) peak should be ≦0.05 and imine ($\delta$ 7.88, t) should be ≧0.95. The imine solution was filtered through a pad of celite (5 mm celite on a 300 mL sintered glass funnel) under a N₂ blanket and held under N₂. $^1$H NMR ($\delta$, CDCl₃): 8.40 (m, 1 H), 7.90 (t, J=4.7 Hz, 1 H), 7.40 (d, J=7.7 Hz, 1 H), 7.07 (dd, $J_1$=7.7 Hz, $J_2$=4.7 Hz, 1 H), 4.32 (t, J=5.4 Hz, 1H), 3.62 (td, $J_1$=7.4 Hz, $J_2$=3.0 Hz, 2 H), 2.95-2.70 (m, 2 H), 2.36-2.28 (m, 1 H), 2.06-1.98 (m, 3 H), 1.86-1.66 (m, 2H, overlapped with THF signal), 1.49 (s, 18 H) ppm.

In a second reaction vessel, anhydrous ZnCl₂ (166 g, 1.5 eq.) was added in portions to THF (800 mL) while cooled in a dry ice/acetone/water bath (≦-20° C.). The rate of addition was controlled to maintain internal temperature at 0~8° C. When all ZnCl₂ had dissolved, solid NaBH₄ (31 g, 1 eq.) was added portion-wise to obtain a slightly turbid solution. The resulting mixture was cooled to -40° C. and the imine solution was introduced slowly while maintaining the internal temperature below -20° C. After the imine addition, the reaction mixture was stirred at -20° C. for 30 minutes, when NMR of an aliquot sample indicated completed reduction. To obtain an aliquot sample for NMR, an aliquot was withdrawn from the reaction vessel and quenched with saturated NH₄Cl solution. The mixture was extracted with dichloromethane, and the organic layer dried under high vacuum, yielding a residue which was checked by NMR.

Saturated NH₄Cl aqueous solution (1/10 of total volume) was added dropwise at -20° C. After the addition, the reaction mixture was warmed up to room temperature while aqueous HCl (3 M) was added to bring the aqueous pH to ~5. The mixture was stirred for 2 hours at room temperature, and then it was partitioned between water (6 L) and dichloromethane (2 L). Saturated NH₄Cl solution (500 mL) and concentrated NH₃.H₂O (500 mL) were added and the mixture was vigorously stirred for 20 min. The organic layer was drained and the aqueous layer was re-extracted with dichloromethane (2 L). The organic layer was combined and the aqueous was discarded.

The organic extract was washed once with a mixture of saturated $NH_4Cl$ (500 mL), concentrated $NH_3.H_2O$ (500 mL), and water (2 L), and once with water (3 L). The organic layer was then stirred with water (2 L) and the pH of the equilibrated aqueous was adjusted to 2 by dilute HCl (1 M). The dichloromethane layer was separated and dried with anhydrous $MgSO_4$ (300 g). The mixture was filtered through a celite pad (1 cm celite on a 2 L sintered glass funnel) and the filter cake was rinsed with dichloromethane (200 mL×2). The filtrate was concentrated to ~1/10 of its original volume, then methyl tert-butyl ether (2 L) was introduced slowly with agitation to induce crystallization. The mixture was gently stirred overnight at room temperature. The precipitate was filtered, washed with methyl tert-butyl ether (500 mL×2) and dried under high vacuum to give the 2°-amine HCl salt 7 as an almost white, low-density powder, 306.45 g (83%, 98% LC). $^1$H NMR ($\delta$, $CDCl_3$): 9.77 (s, br, 2 H), 8.40 (d, J=4.0 Hz, 1 H), 7.50 (d, J=7.5 Hz, 1 H), 7.23 (dd, $J_1$=7.6 Hz, $J_2$=4.6 Hz, 1 H), 4.37 (dd, $J_1$=10.1 Hz, $J_2$=5.4 Hz, 1 H), 3.60 (t, J=7.2 Hz, 2 H), 3.22-3.01 (m, 2 H), 3.00-2.76 (m, 2 H), 2.62-2.50 (m, 1 H), 2.42-2.16 (m, 2 H), 2.02-1.62 (m, 5 H), 1.50 (s, 18 H) ppm; $^{13}$C NMR ($\delta$, $CDCl_3$): 152.5, 149.4, 146.9, 137.8, 133.2, 123.7, 82.3, 57.2, 45.0, 44.3, 27.9, 27.3, 25.8, 24.5, 23.5, 20.0 ppm; MS (M/z): 420, 320, 220.

Alkylation

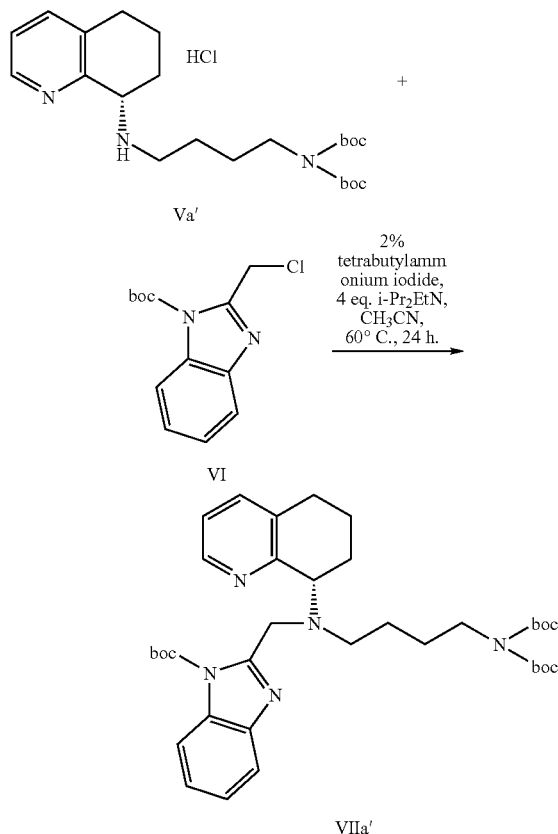

The solid 2°-amine HCl salt (Va') (301.77 g, 0.663 mol) was placed in a 2 L, 3-neck RBF fitted with a mechanical stirrer, a temperature probe, and a nitrogen inlet. $CH_3CN$ (660 mL) was added, and the stirring was started. To this suspension was added i-$Pr_2EtN$ (473 mL, 4 eq.), DMAP (0.02 eq.), and N-Boc-chloromethylbenzimidazole (VI) (185.75 g, 1.05 eq.). The mixture was stirred at 60° C. under $N_2$ until aliquot NMR indicated completed reaction.

All volatiles were removed by rotary evaporation. The residue was partitioned between water (3 L) and EtOAc (2 L). The pH of the aqueous was adjusted to 2-3 with aqueous HCl (6 M). The layers were separated and the aqueous was re-extracted with EtOAc (2 L×2). The organic extracts were combined and concentrated to dryness to give the product as a dark brown thick paste, ~420 g (some solvent remained). This material was used directly in the subsequent reaction without further purifications. $^1$H NMR ($\delta$, $CDCl_3$): 8.34 (d, br, J=4.1 Hz, 1 H), 7.80 (dd, $J_1$=7.4 Hz, $J_2$=4.1 Hz, 1 H), 7.68 (dd, $J_1$=5.8 Hz, $J_2$=3.3 Hz, 1 H), 7.30-7.20 (over lapped with $CHCl_3$ signal, 3H), 6.94 (dd, $J_1$=7.4 Hz, $J_2$=4.6 Hz, 1 H), 4.62 (1/2 AB quartet, J=15.6 Hz, 1 H), 4.45 (1/2 AB quartet, J=15.6 Hz, 1 H), 4.22 (dd, $J_1$=9.6 Hz, $J_2$=5.9 Hz, 1H), 3.40 (t, J=7.0, 2 H), 2.90-2.58 (m, 4 H), 2.20-2.04 (m, 1 H), 2.03-1.78 (m, 3 H), 1.68 (s, 9H), 1.75-1.60 (m, 2H, overlapping with $\delta$1.68 signal), 1.42 (s, 18 H), 1.54-1.24 (m, 2H, overlapping with $\delta$1.42 signal) ppm; MS (M/z): 550, 450, 350.

Deprotection

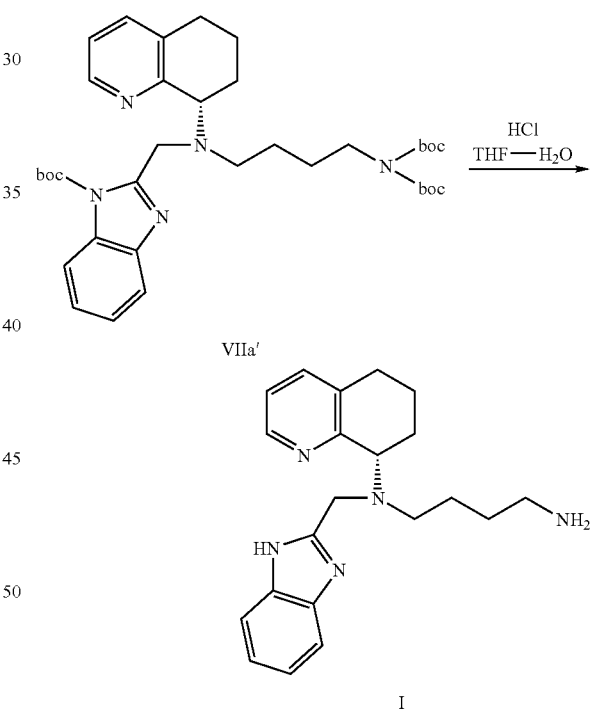

A solution of crude tri-Boc (VIIa') (320 g, ~0.49 mol) in THF (300 mL) was added to aqueous HCl (1 M, 4.4 L) with vigorous stirring. The mixture was stirred at 20° C. for 20 h. An aliquot sample was obtained by partitioning between saturated $Na_2CO_3$ and dichloromethane, extracting the organic layer, and drying under high vacuum to obtain a residue. The residue was taken up with $CDCl_3$ and used for NMR to indicate complete reaction.

The reaction mixture was cooled to 0° C. and adjusted to pH 6 with NaOH (10 M, total 520 mL added). The mixture was extracted with DCM (1.5 L×3). Additional base was added as needed to maintain pH 6. The aqueous was subjected to further decolorization and extractions.

A 2 L portion (expect 77 g product) of the aqueous was treated with charcoal (15.4 g, ~20% w/w of expected product amount) by stirring vigorously under $N_2$ at room temperature for 0.5 hour. The mixture was filtered through a celite pad (5 mm celite on a 350 mL sintered glass funnel), and the filter cake was washed with water (100 mL). The filtrate was adjusted to pH 9-10 with NaOH (4 M) and extracted with DCM (600 mL×2). Additional base was added to maintain the pH during extractions. The combined extract was washed once with NaOH (1 M, 100 mL) and stirred with anhydrous $Na_2SO_4$ (140 g) for 1 hour under $N_2$. The mixture was filtered and the filter cake was washed once with DCM (200 mL). The filtrate was concentrated by rotary evaporation (bath 45° C.). A small amount of iso-propyl acetate (~50 mL) was added and the mixture was re-evaporated until distillation almost stopped. Pre-heated iso-propyl acetate (400 mL, 50° C.) was used to dissolve the residue. A small amount of seed crystals were added and the mixture was allowed to cool to room temperature overnight with vigorous stirring. The precipitate was collected by filtration and was washed once with iso-propyl acetate (50 mL). The filter cake was suction-dried under a stream of $N_2$ and further dried under high vacuum to give compound of Formula I, freebase. Total 60.37 g (78%), white crystalline powders (99.2% by LC-MS, 99.98% e.e.)

EXAMPLE 3

Large Scale Synthesis of —(1H-benzimidazol-2-ylmethyl)-N'-5,6,7,8-tetrahydroquinolin-8-yl-1,4-butanediamine Synthesis of N,N-di-tert-butoxycarbonyl-4-aminobytyraldehyde (IIIa)

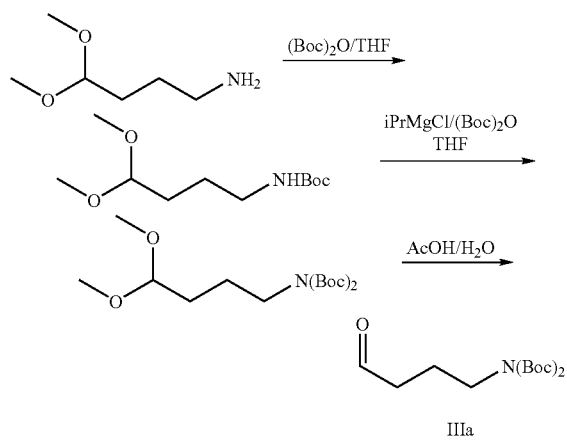

Dimethyl-4-aminobtyraldehyde acetal (670 g, 5.0 mol, 1.0 wt. eq.) was charged to a vessel. THF (1.68 L, 2.5 vol.) was added, and the solution was cooled to 10-15° C. Di-tert-butyl dicarbonate (1.10 kg, 5.0 mol, 1.0 eq., 1.64 wt.) was dissolved in THF (1.00 L, 1.5 wt.) at 0-20° C., and the solution was then added to the solution of the acetal, maintaining an internal temperature of 10-15° C. A line rinse of THF (335 mL, 0.5 vol.) was then done. The solution was then warmed to 15-25° C., and was maintained at this temperature for 30-60 minutes, until the reaction was deemed to be complete by GC or $^1$H NMR (CDCl$_3$). The reaction mixture was then concentrated under vacuum at 15-25° C. to 2 vol (1.35 L). THF (3.35 L, 5 vol.) was then added, and the concentration was repeated. The THF additions and distillations were repeated until the tBuOH level in solution was determined to be <5.0 mol % relative to product.

THF (670 mL, 1.0 vol) was then added, and the solution was cooled to −10° C. isopropylmagnesium chloride (2.0M in THF, 2.76 L, 5.5 mol, 1.1 eq., 4.13 vol) was added to the monoprotected amine at −12° C. to −8° C. over 2-3 hours. A line rinse of THF (330 mL) was then done, and the resulting solution was stirred at −10° C. for 30-40 minutes. A solution of Di-tert-butyl dicarbonate (1.31 kg, 6.0 mol, 1.2 eq., 1.97 wt.) in THF (1.00 L, 1.5 wt.) was then added, maintaining the temperature below −8° C. (over 2-3 hours). The reaction was then stirred at −10° C. until complete by $^1$H NMR (<5 mol % mono-protected amine). The reaction was then warmed to 0-20° C., and was quenched with a solution of potassium sodium tartrate (40% w/w, 5.3 L, 8 vol). After stirring for 30-60 minutes, the layers were separated, and the organic layer was washed with water (2.0 L, 3.0 vol.) The organic layer was then concentrated to 4 vol. (2.7 L) under vacuum at <25° C.

Acetic acid (3.35 L, 5.0 vol) was then added to the di-protected amine solution at 25-30° C. Sodium chloride (67 g, 0.1 wt.) in water (1.68 L, 2.5 vol.) was then added, and the reaction was stirred at 25-30° C. until complete by $^1$H NMR (<8% acetal). A solution of 50% w/w aqueous sodium hydroxide was then added to the solution at <30° C. until the pH was 8-9. Heptanes (2.0 L, 3.0 vol.) was then added, and the layers were separated. As second heptane wash (2.0 L) was performed, and the combined organic layers were dried over anhydrous sodium sulfate, filtered, and concentrated to 3 vol. (2.0 L) at <25° C. The aldehyde solution was stored at 0-5° C. until required. Yield: 1.01 Kg by NMR assay (70% or a solution 78% pure by GC).

Reductive Amination

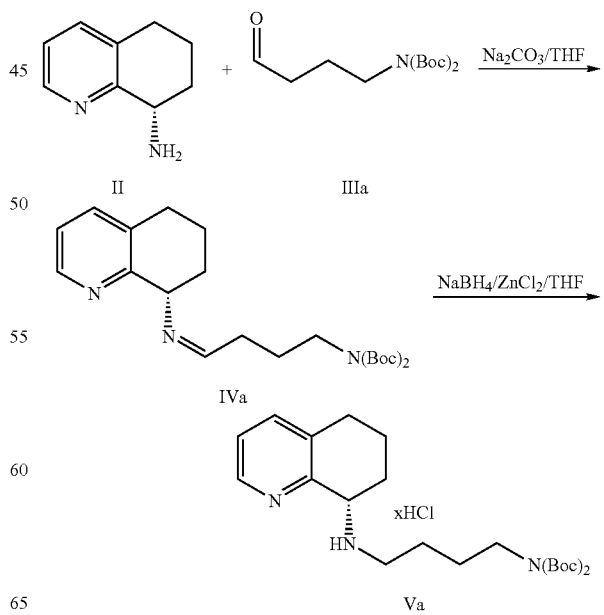

To a solution of the (S)-8-amino-5,6,7,8-tetrahydroquinoline (2.5 mol, 1.0 eq.) in THF (7.5 L, 3 vol) was added sodium carbonate (240 g, 2.5 mol, 1.0 eq.). The solution was cooled to 0-5° C., and the solution of aldehyde IIIa in heptanes (1.0 eq., ca. 3 vol.) was added. The reaction was then warmed to 20-25° C., and was stirred for 1 h. Analysis by $^1$H NMR was used to determine stoichiometry, and the amount of aldehyde required to achieve complete conversion. Extra aldehyde solution was added, as necessary, until completion by $^1$H NMR was achieved (<5% mol aldehyde, >95% mol. imine). The mixture was then filtered, rinsing the filter with THF (2×2.5 L). The imine Iva solution was held at 0-5° C. under nitrogen.

THF (13.75 L,5.5 vol) was added to a vessel, followed by the portionwise addition of zinc chloride (510 g, 3.75 mol), maintaining the temperature below 20° C. The solution was then stirred for 1-2 hours, and sodium borohydride (95 g, 2.5 mol) was added to the solution. The mixture was then stirred for 2-3 hours, before being cooled to −20 to −30° C. The imine solution from above was then added, maintaining the temperature below −20° C. The reaction was then stirred for 1-2 hours at −20 to −30° C., before being checked by $^1$H NMR (<5% imine expected) on an hourly basis. Once the reaction is complete, the solution is added to a 25% w/w aqueous ammonium chloride solution (7.5 L). Dichloromethane (7.5 L) was added as a line rinse. A 6M HCl solution was added until the pH was 4.5 to 5.5. The aqueous and organic layers were then separated, and the organic layer was washed with a mixture of 25% w/w aqueous NH$_4$Cl (7.5 L) and concentrated aqueous ammonia (7.5 L). The layers were then separated, and the wash of the organic layer was repeated, and the layers were once again separated. Water (7.5 L) was then added to the organic layer. 6N HCl was added slowly, with agitation, until the pH of the aqueous layer was 2.0 to 2.5. The layers were then separated, and the aqueous layer was washed with dichloromethane (7.5 L). The organic layers were then combined, and dried with anhydrous sodium sulfate (1.0 kg). The mixture was stirred for approximately one hour, before being filtered. The filtrate was concentrated under vacuum (at 30-35° C.) to a volume of approximately 2 L. TBME (7 L) was added at 30-35° C. at a constant rate over at least two hours to initiate precipitation of the product Va. The slurry was then cooled to approximately −10° C. and was aged for 1-2 hours before being filtered. The filter cake was then washed with TBME (2×1.5 L), and was then dried under vacuum at <50° C. until the residual TBME was <0.1% w/w. The yield of Va was 957 g (2.09 mol, 83% from II).

Alkylation and Deprotection

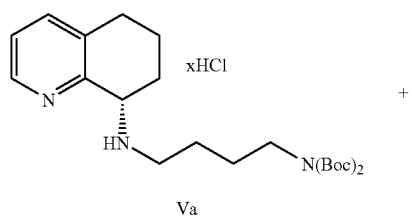

Va

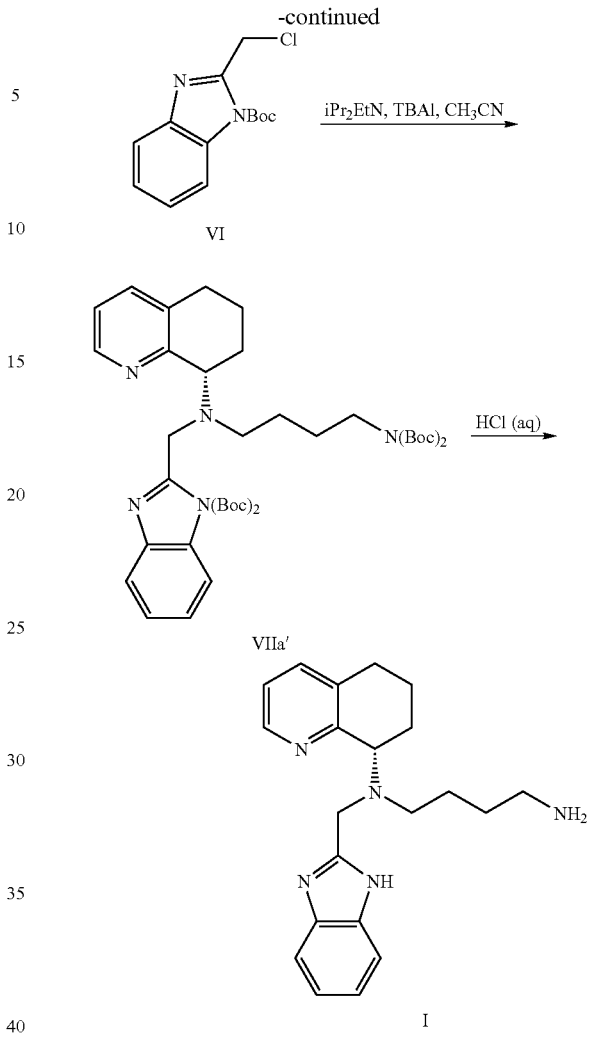

To a vessel was added Va (740 g, 1.63 mol) and tetrabutylammonium iodide (TBAI, 118 g, 0.032 mol, 0.02 eq.), followed by acetonitrile (740 mL). Diisopropylamine (1.15 L, 6.52 mol, 4.0 eq) was then added, and the mixture was heated to 60-65° C. In a second vessel, VI (420 g, 1.60 mol, 0.98 eq.) was dissolved in acetonitrile (800 mL). The solution of VI was then added to the solution of Va, maintaining the temperature at 60-65° C. The reaction was stirred for 1-2 hours, and then the ratio of residual Va to VI was determined by $^1$H NMR. If necessary, extra VI is added to achieve equal stoichiometry between the residual starting materials. The reaction was then stirred until <0.35% mol residual VI is achieved by $^1$H NMR.

The reaction was then cooled to 20-25° C. Concentrated commercial ammonium hydroxide (225 mL) was then added, and the reaction was stirred at 20-25° C. for 1 hour. Water (750 mL) was then added to the reaction mixture, and the biphasic mixture was then added to a separate vessel containing HCl (35% w/w, 1.5 L). Acetonitrile (750 mL) was then used as a line rinse. The reaction was then stirred at 35-40° C. until complete by $^1$H NMR. Water (2.25 L) was then added, and the mixture was distilled under reduced pressure at 30-40° C. to approximately 3 L. The level of acetonitrile was determined by NMR (if >3% w/w, more water is added, and the distillation is repeated).

The mixture was then cooled to 15-25° C., and dichloromethane (1.5 L) is added. The pH of the aqueous layer was adjusted to >12.5 by the addition of 25% w/w aqueous sodium hydroxide. The solution was then air sparged for 2-2.5 hours at 15-25° C. The pH of the aqueous layer was adjusted to 5.0-5.5 with 6N HCl, and the layers were separated. The yield of the reaction, as determined by $^1$H NMR assay, was 82%. The aqueous layer could then be treated with charcoal and carried forward to the freebase crystallization as per Example 2.

It is understood that the examples and embodiments described herein are for illustrative purposes only and that various modifications or changes in light thereof will be suggested to persons of skill in the art and are to be incorporated within the spirit and purview of this application and the scope of the claims. All publications, patents, and patent applications cited herein are hereby incorporated by reference.

Citation of the above documents is not intended as an admission that any of the foregoing is pertinent prior art, nor does it constitute any admission as to the contents of date of these documents.

What is claimed is:

1. A process for synthesizing a product having Formula I',

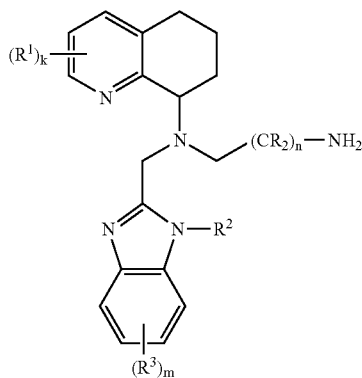

I' wherein each R, $R^1$, $R^2$ and $R^3$ is independently selected from the group consisting of halo, nitro, cyano, carboxylic acid, hydroxyl, thiol, amino, acyl, carboxylate, carboxamide, sulfonamide, and a heterocyclic group; or alkyl ($C_{1-10}$), alkenyl ($C_{2-10}$), alkynyl ($C_{2-10}$), aryl ($C_{5-12}$), arylalkyl, arylalkenyl, and arylalkynyl, each of which may optionally contain one or more heteroatoms selected from O, S, and N; or each R and/or $R^2$ can independently be H; k is 0-3; m is 0-4 and n is 1-6, comprising:

(a) reacting a 5,6,7,8-tetrahydroquinolinylamine optionally substituted with $R^1$ with an alkyl aldehyde bearing a phthalimide protecting group or a di-tert-butoxycarbonyl protecting group to produce an imine;

(b) reducing the imine in an organic solvent with a metal hydride reducing reagent and either an organic acid or a metal salt to form a secondary amine;

(c) reacting the secondary amine with a 2-halomethyl-benzimidazole optionally substituted with $R^3$ and optionally bearing a benzimidazole amine protecting group or other amine substitution ($R^2$) to form a phthalimido-protected or a di-tert-butoxycarbonyl-protected tertiary amine; and (d) hydrolyzing the protected tertiary amine to obtain the product of Formula I'.

2. The process of claim 1, further comprising treating the product of Formula I' obtained in step (d) with decolorizing carbon or silica gel to remove impurities.

3. The process of claim 1, wherein said 5,6,7,8-tetrahydroquinolinylamine is a racemic mixture.

4. The process according to claim 3, wherein the product of Formula I' is a racemic mixture.

5. The process of claim 4, further comprising isolating an (R) or (S) enantiomer of the product of Formula I' via selective crystallization in a crystallization solvent, wherein the product of Formula I' is a crystalline product.

6. The process of claim 1, wherein said 5,6,7,8-tetrahydroquinolinylamine is an optically active (S) enantiomer.

7. The process of claim 6, wherein the product of Formula I' is an optically active (S) enantiomer.

8. The process of claim 1, wherein said 5,6,7,8-tetrahydroquinolinylamine is an optically active (R) enantiomer.

9. The process of claim 8, wherein the product of Formula I' is an optically active (R) enantiomer.

10. The process of claim 1, wherein k and m are 0 and R and $R^2$ are H.

11. The process of claim 1, wherein each R, $R^1$, $R^2$ and $R^3$ is independently selected from the group consisting of alkyl ($C_{1-10}$), alkenyl ($C_{2-10}$), alkynyl ($C_{2-10}$), aryl ($C_{5-12}$), arylalkyl, arylalkenyl, and arylalkynyl, each of which may optionally contain one or more heteroatoms selected from O, S, and N; or each R and/or $R^2$ can independently be H.

12. The process of claim 11, wherein at least one of R, $R^1$, $R^2$ and $R^3$ contain one or more heteroatoms selected from the group consisting of O, S, and N.

13. The process of claim 1, wherein the alkyl aldehyde is an ethyl aldehyde, a propyl aldehyde, a butyl aldehyde or a pentyl aldehyde.

14. The process of claim 1, wherein the dehydrating agent in step (a) is potassium carbonate, sodium carbonate, sodium bicarbonate or magnesium sulfate.

15. The process of claim 1 wherein the reducing agent in step (b) is sodium borohydride, and the organic acid is selected from the group consisting of acetic acid, propionic acid and zinc chloride.

16. The process of claim 1, wherein step (b) is performed at a reduced temperature of −25 to −5° C.

17. The process of claim 1, wherein the organic solvent in step (c) further comprises an amine base and a catalytic amount of iodide.

18. The process of claim 17, wherein the amine base is diisopropylethylamine.

19. The process of claim 1, wherein the elevated temperature in step (c) is 40-60° C.

20. The process of claim 1, wherein $R^2$ is a t-butoxycarbonyl amine protecting group.

21. The process of claim 20, wherein removal of the amine protecting group in step (d) is performed at a pH 3 under aqueous conditions.

22. The process of claim 1, wherein removal of the phthalimide protecting group in step (d) is performed with hydrazine, ethylene diamine, n-butylamine or methylamine.

23. The process of claim 1, further comprising a purification step (e) purifying the product of Formula I'.

24. The process of claim 23, wherein step (e) comprises extracting the product of Formula I' into a mildly acidic aqueous solution followed by treatment with an activated carbon.

25. The process of claim 23, wherein step (e) comprises treating an organic solution of the product of Formula I' with activated carbon followed by filtrating and extracting into a mildly acidic aqueous solution.

26. The process of claim 23, wherein step (e) includes extracting a basic aqueous solution of the product of Formula I' with dichloromethane, followed by silica gel flash chromatography.

27. The process of claim 23, wherein step (e) includes extracting a dichloromethane solution of the product of Formula I' with aqueous sodium hydroxide.

28. The process of claim 5, wherein the crystallization solvent is isopropyl acetate.

29. The process of claim 5, wherein the crystallization solvent is ethyl acetate, tetrahydrofuran or dichloromethane.

30. The process of claim 5 further comprising the step of concentrating the product of Formula I' to dryness prior to the crystallization step.

31. The process of claim 5, wherein the crystallization solvent is isopropyl acetate or ethyl acetate, and the crystallization step is performed at a temperature of 50-65° C. to achieve solvation with the crystallization solvent.

32. The process of claim 5, wherein the crystallization step further comprises seeding a solution of the product of Formula I' with crystalline Formula I' to initiate crystallization.

33. The process of claim 5, wherein the crystallization step is performed while agitating a solution of the product of Formula I' to control particle size of the Formula I' crystals.

34. The process of claim 5, wherein the crystalline product of Formula I' is dried in a vacuum oven to lower residual solvent levels.

35. The process of claim 1, wherein the product of Formula I' is selected from the group consisting of (S)—N'-(1H-benzimidazol-2-ylmethyl)-N'-5,6,7,8-tetrahydroquinolin-8-1,4-butanediamine; (R)—N'-(1H-benzimidazol-2-ylmethyl)-N'-5,6,7,8-tetrahydroquinolin-8-yl-1,4-butanediamine; and (R,S)—N'-(1H-benzimidazol-2-ylmethyl)-N'-5,6,7,8-tetrahydroquinolin-8-yl-1,4-butanediamine.

36. The process of claim 1, wherein said secondary imine is N-[(1,3-dioxo-1,3-dihydroisoindol-2-yl)-alkyl)]-tetrahydroquinolinylamine, (S)-2-[4-(5,6,7,8-tetrahydroquinolin-8-ylamino)-butyl]-isoindole-1,3-dione; (R)-2-[4-(5,6,7,8-tetrahydroquinolin-8-ylamino)-butyl]-isoindole-1,3-dione; (R,S)-2-[4-(5,6,7,8-tetrahydroquinolin-8-ylamino)-butyl]-isoindole-1,3-dione; or an imine having the formula

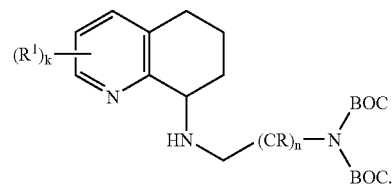

37. The process of claim 1, wherein the phthalamido-protected tertiary amine compound is N-{[(benzimidazol-2-yl)methyl-(1,3-dioxo-1,3-dihydroisoindol-2-61)-alkyl]-tetrahydroquinolinyl}amine; (S)-2-{4-[(1H-benzimidazol-2-ylmethyl)-(5,6,7,8-tetrahydroquinolin-8-yl)-amino]-butyl}-isoindole-1,3-dione; (R)-2-{4-[(1H-benzimidazol-2-ylmethyl)-(5,6,7,8-tetrahydroquinolin-8-yl)-amino]-butyl}-isoindole-1,3-dione; or (R,S)-2-{4-[(1H-benzimidazol-2-ylmethyl)-(5,6,7,8-tetrahydroquinolin-8-yl)-amino]-butyl}-isoindol-1,3-dione.

38. The process of claim 1, wherein the di-tert-butoxycarbonyl-protected tertiary amine has the formula

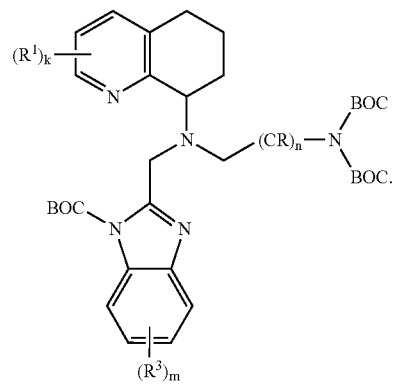

* * * * *